United States Patent [19]
Khutoryansky et al.

[11] Patent Number: 5,751,788
[45] Date of Patent: *May 12, 1998

[54] UNIVERSAL RADIOGRAPHIC/ FLUOROSCOPIC DIGITAL ROOM

[75] Inventors: Oscar Khutoryansky; Dennis Bleser; Allan Kojro, all of Glenview; Thomas Simak, Warrenville; Thomas Rosevear, Forest Park, all of Ill.

[73] Assignee: Continental X-Ray Corporation, Broadview, Ill.

[ * ] Notice: The term of this patent shall not extend beyond the expiration date of Pat. No. 5,636,259.

[21] Appl. No.: 729,989

[22] Filed: Oct. 11, 1996

Related U.S. Application Data

[63] Continuation of Ser. No. 443,486, May 18, 1995, Pat. No. 5,636,259.

[51] Int. Cl.$^6$ .................................................... H05G 1/02
[52] U.S. Cl. ........................ 378/197; 378/196; 378/205
[58] Field of Search ............................ 378/62, 193, 196, 378/197, 167, 177, 205

[56] References Cited

U.S. PATENT DOCUMENTS 4,211,927  7/1980  Hellstrom et al. .................. 378/197 X
4,807,273  2/1989  Haendle ................................ 378/197

*Primary Examiner*—David P. Porta
*Attorney, Agent, or Firm*—Laff, Whitesel, Conte & Saret, Ltd.

[57] ABSTRACT

A universal radiographic/fluoroscopic "room" is constructed according to the present invention by combining a versatile group of X-ray examination system components, electrical and mechanical drive components, and sensing components, under the supervision of a flexible control system, to form a universal diagnostic medical imaging system capable of performing radiographic, fluoroscopic, tomographic, and stepped examinations in several different operator-selectable configurations. The operator selects any available operating mode, including auto-bucky, auto-wall, auto-table, auto-table/wall, servo-tomo, conventional stepping, stepped-digital, auto-step, and auto-step-center modes, using a a control panel. The control system automatically determines which system components are required to perform that type of examination, moves the components into operational or storage positions as required, and prepares each component for operation. The operator need not manually reconfigure the equipment. In "stepped-digital" modes useful for peripheral angiography, an under-table X-ray tube and over-table image intensifier execute a series of radiographic exposures at preselected locations. The digital imaging platform is moved while the patient remains stationary. This reduces motion artifacts. For each step, a test fluoroscopic exposure is performed under automatic brightness control to determine an optimum technique. The technique so determined is converted for use in a subsequent radiographic exposure. The operator observes the flow of the contrast medium during the test fluoroscopic exposure and commands the radiographic exposure when the contrast medium arrives at the desired position in the image. Alternatively, the control system may detect the presence of the contrast medium in the image by comparing a change in image contrast with a previously observed threshold change.

4 Claims, 30 Drawing Sheets

AUTO BUCKY MODE

AUTO TABLE MODE

AUTO TABLE/WALL MODE

SERVO TOMO MODE

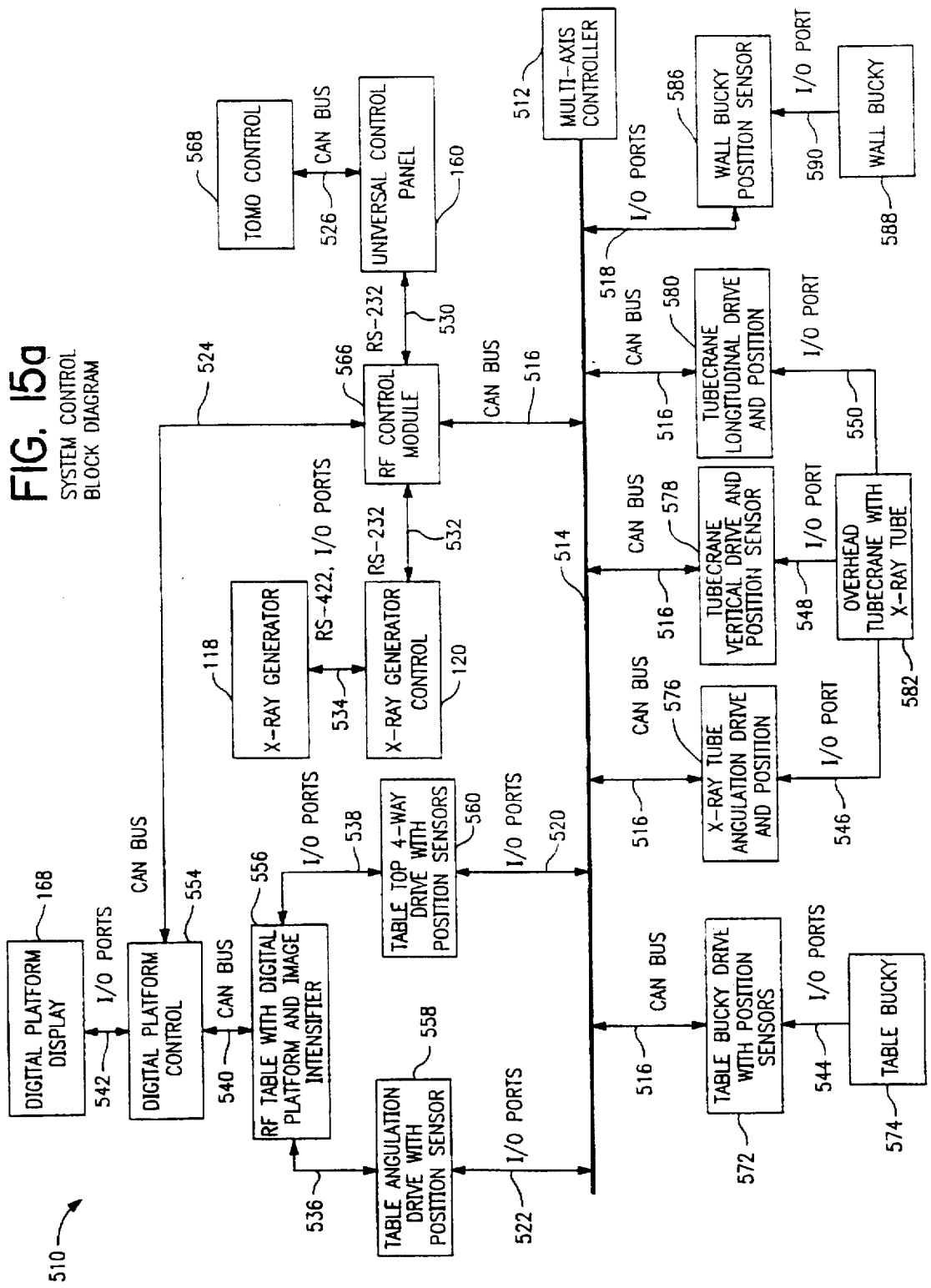

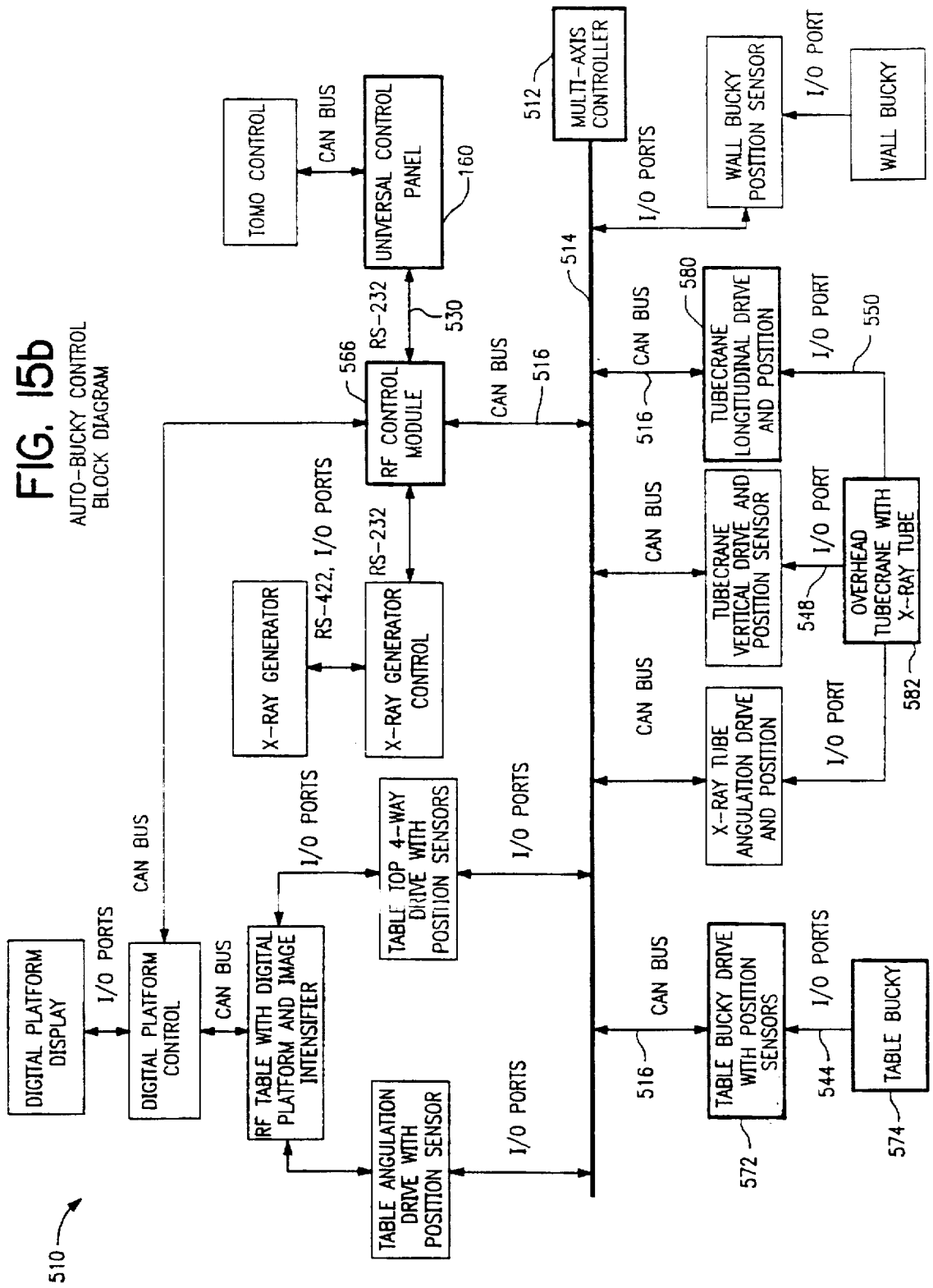

AUTO-BLOCK CONTROL BLOCK DIAGRAM

AUTO-WALL CONTROL BLOCK DIAGRAM

SERVO TOMO CONTROL
BLOCK DIAGRAM

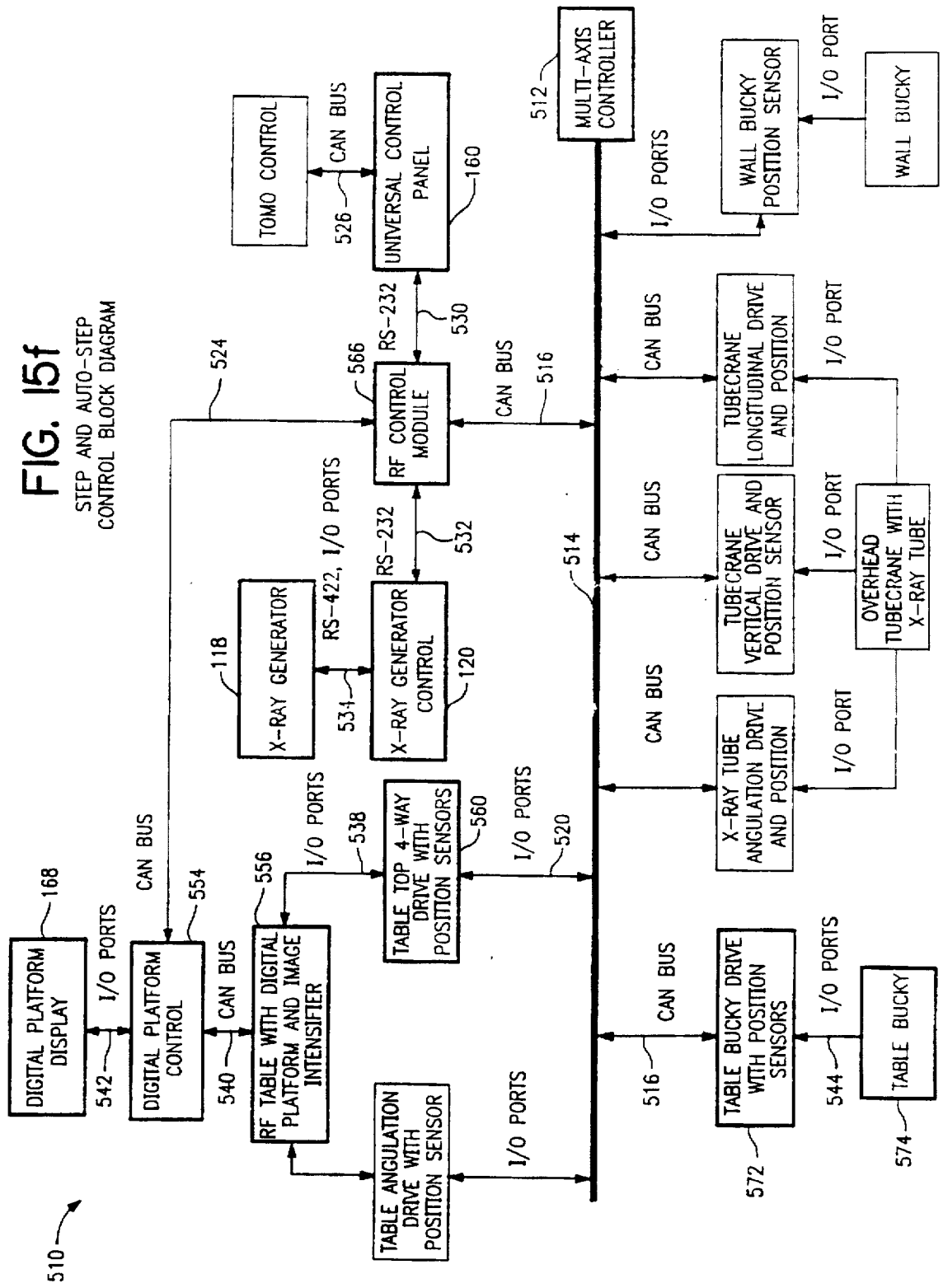

DIGITAL CONTROL STEPPING SETUP

DIGITAL CONSOLE STEPTOP DISPLAY

DIGITAL CONSOLE COLLIMATOR DISPLAY

AUTO STEP MODE

"AUTO STEP CENTER" MODE

UNIVERSAL RADIOGRAPHIC/FLUOROSCOPIC DIGITAL ROOM

This application is a continuation of prior application Ser. No. 08/443,486, filed May 18, 1995 now U.S. Pat. No. 5,636,259.

BACKGROUND OF THE INVENTION

This invention relates to medical diagnostic imaging systems, and more particularly, to apparatus and methods for providing a highly versatile diagnostic medical imaging system capable of performing a plurality of different penetrating radiation imaging examinations, including radiographic, fluoroscopic, tomographic, and stepped radiographic/fluoroscopic examinations.

A wide spectrum of equipment is now commercially available for performing diagnostic medical imaging examinations using penetrating radiation or electromagnetic fields. Although there is great diversity in complexity, application, and cost, among the available commercial products, a significant problem for many users of diagnostic imaging equipment is the lack of a general-purpose, highly versatile platform for efficiently conducting a variety of different types of examinations while producing high quality results.

There are, for example, several fairly recently developed imaging modalities (such as Magnetic Resonance Imaging, Computed Tomography, Positron Emission Tomography, etc.), which provide images of high diagnostic quality. However, these devices rely on elaborate arrays of mechanical equipment, radiation or field detectors, and computers and signal processors, and therefore, they are expensive to purchase and operate. This expense is reflected in the fees charged to patients, either directly or indirectly, when they are examined. As a result, although these newer imaging modalities may be generally useful, there is substantial pressure on health care providers to order such examinations only when conventional imaging modalities cannot be used. This class of imaging equipment has therefore become highly specialized because each system is narrowly directed to a single imaging modality, and because their high cost prevents their general application to run-of-the-mill imaging.

Other relatively specialized equipment has been developed to accomplish more conventional imaging examinations. Fluoroscope systems often lack facilities for conventional radiographic examinations. Conventional linear tomography systems typically have mechanical couplings between an X-ray source and a film holder or other image receiver, and these couplings may make it difficult to use such systems for general purpose radiography. Even when multiple purpose imaging systems have been provided in the past, it has been relatively difficult and time consuming to convert such systems from one imaging mode to another. This undesirably decreases the flexibility of the imaging system, and increases the cost of examinations provided thereby.

Another problem to which the present application is directed is providing high quality peripheral angiography examinations. Peripheral angiography is a diagnostic roentgenographic procedure providing visualization and recording of the blood vessels in the peripheral region of the body, such as the arms and legs. In a typical peripheral angiography examination, a radiopaque contrast agent is injected into a blood vessel, and a rapid sequence of radiographs are taken to observe the progress of the contrast agent as it flows through the vessels along the length of the extremity. The contrast agent is initially concentrated in the blood vessels and takes some time to diffuse generally into the surrounding regions. Thus, the contrast agent renders the blood vessels visible under radiography provided that the radiographs are taken very soon after the contrast agent arrives in a particular region. In conventional Peripheral Angiography examinations, the patient is supported on a movable table top positioned under system control. The table top, in turn, is supported by a stationary radiographic-fluoroscopic table. An overhead X-ray source (which may be mounted on a tube crane) directs a beam through the patient to a "rapid film changer" device.

The locations of interest at any particular time during the examination are in the general vicinity of the leading edge of the contrast material as it progresses though the extremity. In conventional peripheral angiography systems, the rapid film changer is normally in a fixed position. Because the length of the recording radiographic film or imaging device is not sufficient to cover the entire extremity, conventional peripheral angiography systems require that the patient be rapidly repositioned throughout the procedure to fully visualize and record the contrast material as it progresses through the vessels of the extremity (i.e., the patient must be rapidly repositioned throughout the procedure to maintain the contrast material within in the field of view of the rapid film changer). In such conventional systems, the patient rests on a movable table-top, which may travel as rapidly as 9 in/sec between exposures.

Conventional peripheral angiography systems exhibit several disadvantages which reduce the quality of the examinations provided thereby. The position and stability of the patient during the exposure which produces an angiogram is very critical. Even slight movement of the patient contributes to film blur and reduces the diagnostic quality of the examination. The above-mentioned conventional equipment moves the table top supporting the patient very rapidly between exposures. This adds to patient discomfort and may cause motion artifacts.

Another disadvantage of conventional peripheral angiography examination systems is that the typical image recording apparatus (a rapid film changer) is not adapted for automatic exposure controls. The exposure "technique" (that is, exposure parameters such as exposure time and X-ray tube voltage and current) is vital to the success of a peripheral angiography examination. It is often desirable to conduct a study of the entire leg of a patient. Since some portions of the leg are substantially thicker than others, the exposure parameters must be modified during the examination. As a result, the operator must accurately predict and preset the exposure parameters required for each examination step. Although some operators perform a test exposure before injecting the contrast agent, the contrast agent itself varies the radiographic density of the region under study, and it is difficult to adjust in advance the exposure parameters to compensate for this.

For useful results, a peripheral angiography examination requires perfect coordination and timing. Following the injection of the contrast medium, there is only a very short interval in which to maneuver the necessary equipment into place, adjust controls, and change the exposure factors. For example, in some examinations a delay of even one second in making the exposure may render the projection valueless. The operator must calculate in advance the rate of injection, and the speed of the contrast medium flow, and must select in advance the number of steps to be taken, their positions, and the time to progress the next step. Thus, a further disadvantage of conventional peripheral angiography examination systems is that such systems require the operator to plan the coordination of each step in advance, and the systems provide little assistance to the operator. The usual method of assuring that a complete examination will be performed is to perform plural overlapping exposures. This undesirably increases the radiation does received by the patient, and drives up the cost and time required for the examination.

Another disadvantage of the conventional peripheral angiography examination equipment is that the rapid film changer is placed in a fixed position under the table top. Therefore, the table cannot be tilted as is desirable to control the gravitational flow of the contrast medium.

OBJECTS AND SUMMARY OF THE INVENTION

It is therefore an object of the present invention to provide a general-purpose, highly versatile platform for efficiently conducting a variety of different types of diagnostic imaging examinations while producing high quality results.

It is another object of the present invention to provide a universal radiographic/fluoroscopic examination system capable of performing a plurality of different penetrating radiation imaging examinations.

It is a further object of the present invention to provide a universal radiographic/fluoroscopic examination system which includes facilities for performing radiographic, fluoroscopic, tomographic, and stepped radiographic/fluoroscopic examination modes, and provides rapid operator-selectable changeover from one mode to another.

It is another object of the invention to provide a peripheral angiography examination system in which the patient may remain substantially stationary during an examination.

It is a further object of the invention to provide a peripheral angiography examination system which automatically determines an optimum combination of exposure parameters.

It is another object of the invention to provide a peripheral angiography examination system for which the timing of examination steps need not be accurately planned in advance.

A universal radiographic/fluoroscopic "room" is constructed according to the present invention by combining a versatile group of X-ray examination system components, electrical and mechanical drive components, and sensing components, under the supervision of a flexible control system, to form a universal diagnostic medical imaging system capable of performing radiographic, fluoroscopic, tomographic, and stepped examinations in several different operator-selectable configurations. The imaging system comprises a ceiling mounted tube crane driven in at least two dimensions, an X-ray tube supported by the tube crane and mounted for driven rotation about an axis, a driven tiltable patient support table, a driven table top movable in at least two dimensions, an imaging media cassette housed in the patient support table and driven in at least one dimension, an additional imaging media cassette mounted for vertical translation, a digital imaging platform mounted for longitudinal translation along the table and having an under-table X-ray tube and an opposed image intensifier, and a suitable control system capable of simultaneously coordinating movement along at least four axes.

Advantageously, the imaging system provides several examination modes, any of which may be selected by an operator using a control panel. When the operator selects a particular examination mode, the control system automatically determines which system components are required to perform that type of examination, moves the components into operational or storage positions as required, and prepares each component for operation. As a result, the operator need not expend time or effort reconfiguring the system when switching from examination to examination, and patients need not wait for such reconfiguring. This feature dramatically improves the efficiency with which examinations may be conducted.

In an "auto-bucky" mode, the overhead tube crane and table-mounted bucky are used for radiographic exposures; the operator selects the imaged region by directing the tube crane, and the system moves the bucky to an appropriate corresponding position.

In an "auto-wall" mode, the overhead tube crane and wall-mounted bucky are used for radiographic exposures; the operator selects the imaged region by moving the wall-mounted bucky, and the system moves the tube crane to an appropriate corresponding position.

In an "auto-table" mode, the overhead tube crane and table-mounted bucky are used for radiographic exposures; the operator instructs the system to tilt the patient support table to a desired angular position; and the system moves the tube crane to an appropriate corresponding position to maintain the X-ray beam perpendicular to the bucky and to maintain a desired source-image-distance.

In an "auto-table/wall" mode, the overhead tube crane and table-mounted bucky are used for radiographic exposures. The patient support table is tilted to a vertical position; the operator selects the imaged region by directing the tube crane, and the system moves the bucky to an appropriate corresponding position.

In a "servo-tomo" mode, the overhead tube crane and table-mounted bucky are used for a linear tomographic examination; the operator identifies a tomographic fulcrum location within the patient; the system moves both the tube crane and the bucky in opposed, coordinated, but non-mechanically-interlocked motion to achieve a linear tomographic exposure.

In a conventional stepping mode, the overhead tube crane and a fixed, under-table rapid film changer device is used to perform a series of radiographic exposures at predefined patient positions; the system rapidly positions the patient (resting on a movable table surface) in the desired locations over the rapid film changer between exposures.

In "stepped-digital" modes, the under-table X-ray tube and over-table image intensifier are used to execute a series of radiographic exposures at a set of locations previously selected by the operator and using operator-selectable technique. The digital imaging platform may be moved longitudinally along the table under system control to accomplish an examination while the patient remains stationary. This reduces motion artifacts. In a first automatic mode ("auto-step"), a test fluoroscopic exposure is made before each radiographic exposure, and an automatic brightness control is used to determine the optimum technique. The optimum fluoroscopic technique is then converted for use in the radiographic exposure. The radiographic exposure is performed upon operator command, which may occur, for example, when the operator observes that injected contrast medium has arrived in a desired portion of the fluoroscopic image.

A second automatic mode ("auto-step-center") operates similarly, but the difference in image contrast between an original image and the contrast-medium-in-position image is recorded, and that difference is used as a threshold to determine automatically when the contrast medium has arrived, in response, to automatically command the radiographic exposure. These features improve patient safety, examination quality, and efficiency, in particular, for peripheral angiography examinations, because it is no longer necessary for the operator to accurately predict the rate of contrast medium movement, to manually compensate exposure technique for variations in radiographic density, to conduct multiple overlapping exposures, or to repeat examinations.

BRIEF DESCRIPTION OF THE DRAWINGS

These and other features of this invention will be best understood by reference to the following detailed description of a preferred embodiment of the invention, taken in conjunction with the accompanying drawings, in which:

FIG. 15a is a block diagram of an exemplary control system for use in conjunction with the inventive Universal Room of FIG. 1;

FIG. 15b is a block diagram of the exemplary control system of FIG. 15a for use in conjunction with the inventive Universal Room of FIG. 1, in which the control components used in providing real-time control for the "auto-bucky" mode of FIG. 8 are emphasized for clarity;

FIG. 15f is a block diagram of the exemplary control system of FIG. 15a for use in conjunction with the inventive Universal Room of FIG. 1, in which the control components used in providing real-time control for the "digital stepping" and "film-changer stepping" modes of FIGS. 13 and 14 are emphasized for clarity;

Figure 17:
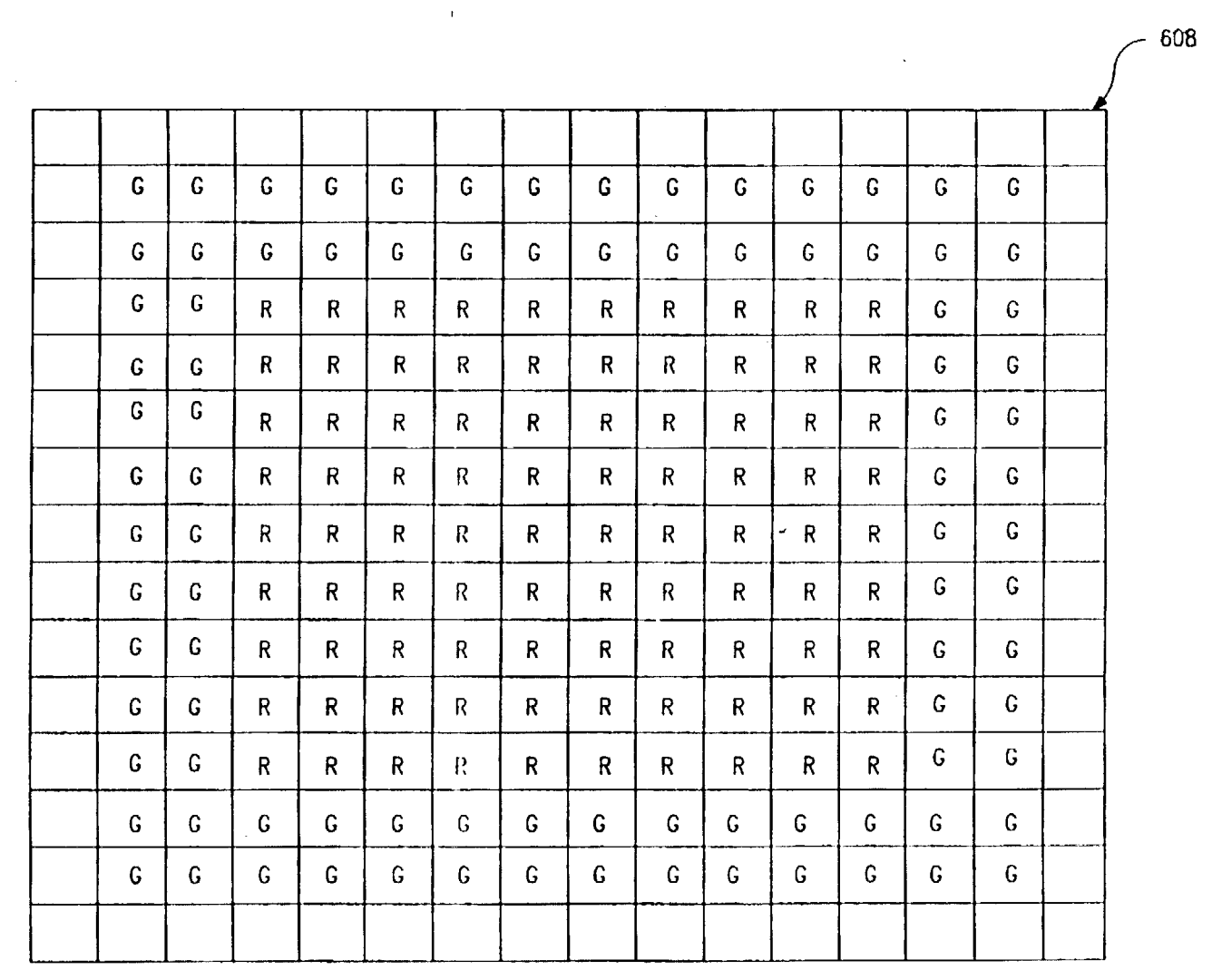

FIG. 17 is a diagram showing the contents of a display provided by the control panel of FIG. 16 to enable an operator to select the size of a collimator opening;

Figure 18:
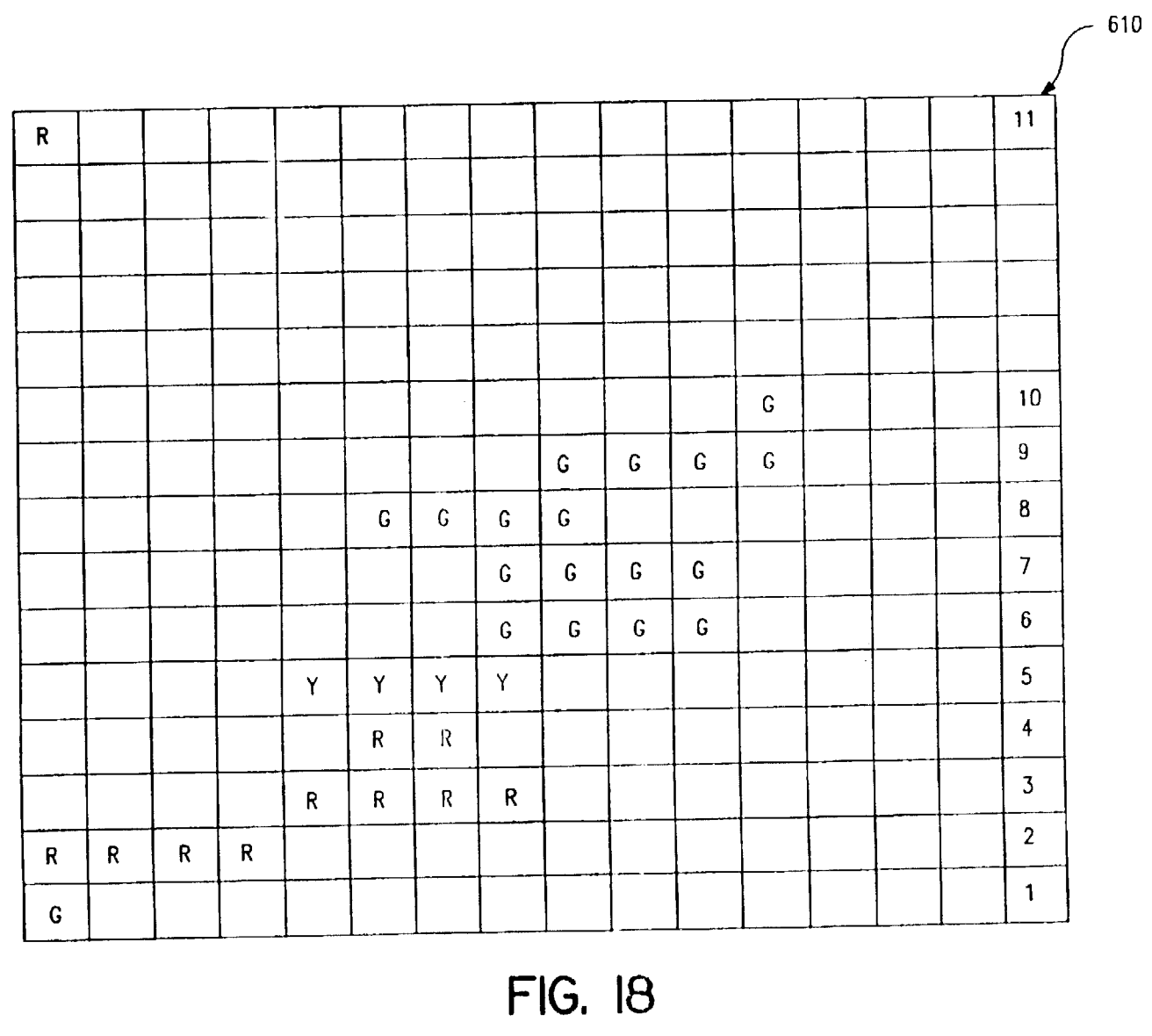

FIG. 18 is a diagram showing the contents of a display provided by the control panel of FIG. 16 to enable the operator to enter a selection for the location and size of each imaging step to be conducted during a combined fluoroscopic and radiographic "step" examination;

DETAILED DESCRIPTION OF THE PREFERRED EMBODIMENT

A preferred embodiment 100 of a Universal Room constructed according to the present invention is shown generally in FIGS. 1–23. The term "Room" as used herein to refer to the invention denotes a versatile suite or combination of mechanical, electrical, and control components, which are located in substantial proximity and which function in a coordinated fashion to perform a variety of radiographic, fluoroscopic, and tomographic examinations as selected by an operator. Because medical imaging equipment requires structural support and generates penetrating radiation, in commercial applications it is often enclosed in an examination room having sturdy wall, ceiling, and floor structures constructed of a radiation shielding material, and this discussion of the preferred embodiment of the invention assumes that it will be applied in such an environment. However, the invention is not limited to application in this environment, and could be used in other environments (such as a military field hospital) if suitable structural supports and radiation shielding are provided.

In addition, although this application describes the present invention in medical imaging applications in which the images are produced using X-radiation, it will be appreciated that the present invention may also be advantageously used in applications in which images are obtained using any suitable type of penetrating radiation, or any other particle, wave, or field phenomenon.

FIGS. 1–14 relate primarily to the mechanical configuration of the Universal Room 100. FIGS. 15a–15f (referred to in gross as "FIG. 15" ) are block diagrams of a control system 510 constructed according to he present invention for coordinating the operation of the electrical and mechanical components of the Universal Room 100. FIGS. 16–18 are diagrams of a control panel 168 for use by an operator in conjunction with the control system 510 and related components to select operational characteristics of the Universal Room. Figs. FIGS. 19–23 are flow diagrams showing methods for controlling the Universal Room 100 and may be used in conjunction with the control system 510 of FIG. 15, and the control panel of FIGS. 16–18. For convenient reference, a set of orthogonal coordinate axes, labelled X, Y, is defined. References herein to the X, Y, or Z directions mean a direction parallel to the respective coordinate axis.

Figure 1:
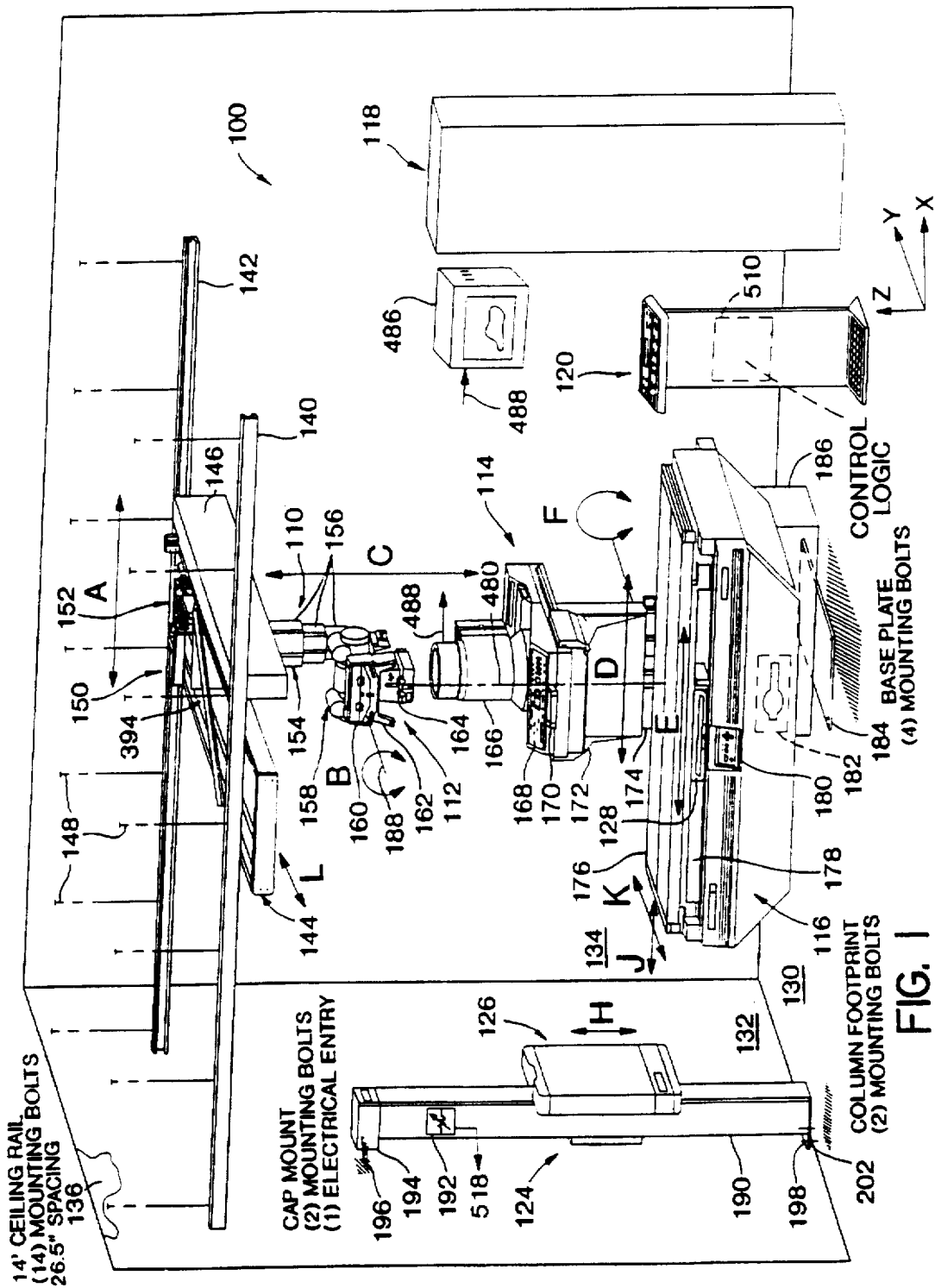
FIG. 1 is a partially exploded oblique perspective view of a Universal Radiographic/Fluoroscopic Room ("Universal Room") constructed according to the present invention.

As best seen in FIG. 1, a preferred embodiment 100 of a Universal Room constructed according to the present invention may be housed in an examination room having a floor 130, a ceiling 136, a side wall 132, a rear wall 134, and additional walls (not shown), or equivalent support members having sufficient structural strength to bear the weight of the various components of the invention.

As best seen in FIG. 1, Universal Room 100 preferably comprises several major functional components: an X-ray tube head 112 supported from the ceiling 136 by a tube crane 110; a floor-mounted examination table 116 for supporting a patient (not shown) and an imaging media cassette 128 (referred to as a "bucky") during examination; a digital imaging platform 114 supported by table 116; a wall mounted fixture 124 for supporting an additional imaging media cassette or bucky 126; an X-ray generator 118; and a main control panel 120 including a control system 510.

Certain of these components are movable in various directions in translation or rotation as indicated by the motion arrows A–H, and K–L. Some of these movements are performed manually by the operator. Other component movements are mechanically powered. The mechanically powered movements may be directed either by an operator (i.e., the movements are "power assisted"), or by the system controller in order to perform a particular imaging examination.

Tube crane assembly 110 supports the X-ray tube head 112 and provides translational movement of the X-ray tube head 112 in the longitudinal (X) direction shown by arrow A, the transverse (Y) direction shown by arrow L, and the vertical (Z) direction shown by arrow C. The tube crane assembly 110 comprises several cascaded mechanical stages, including a transverse carriage 394, a bridge 144, and a telescoping tube assembly 154, each of which permits movement of the X-ray tube head 112 in one of the aforementioned directions.

First and second spaced parallel support channels or rails 140 and 142 preferably extend longitudinally along the ceiling 136 and are attached thereto by a plurality of fastening means 148. The support rails 140 and 142 support a bridge 144 (FIGS. 1, 2, and 4), permitting longitudinal movement of the bridge 144 and everything it supports, as shown by the arrow A. The bridge 144, in turn, supports a transverse carriage 394 (FIG. 1, 2, and 4), permitting transverse movement of the bridge and everything it supports, as shown by the arrow L. The transverse carriage 394 (FIGS. 1, 2, and 4), in turn supports the X-ray tube head 112 by means of a telescoping tube assembly 154 which effectively functions as a vertically oriented linear bearing. The telescoping tube assembly 154 may be formed from a plurality of nested tubular structural members 156 having bearings to allow longitudinal slidable movement therebetween. Thus, the transverse carriage 394 and telescoping tube assembly 154 permit vertical movement of the X-ray tube head 112, as shown by the arrow C.

Movements along directions A and C are powered by a longitudinal drive 150 (FIGS. 1, 2, and 4) and a vertical drive 152 (FIGS. 1, 2, and 4) respectively. Drives 150, 152, which will be discussed further in greater detail, are controlled by system controller 510 (FIGS. 1 and 15), and are preferably housed in the transverse carriage 394. Movements along directions A and C may also be performed manually by the operator. Transverse movement of the tube crane along direction L is not driven, and may only be accomplished manually by the operator.

The X-ray tube head 112 preferably comprises an X-ray tube head rotational drive 270 (FIG. 3), an X-ray tube assembly 158, an X-ray collimator 164, a control panel 160, and control handles 162, 316 for use by the operator in selecting the position of the X-ray tube head 112. Information obtained from control panel 160 is preferably communicated to the system controller 510, which produces control signals to tube crane longitudinal and vertical drives to move the X-ray tube head 112 in the desired direction.

The X-ray tube head 112 is mounted on the telescoping tube assembly 154 for rotation about a transverse axis 188 as shown by the arrow B. Projection line 480 depicts the path of X-rays emitted by the X-ray tube head below collimator 164. Rotation of the X-ray tube head 112 allows the X-ray beam to be directed at various desired angles, such as toward the table 116 (which itself may rotate and translate) or the wall-mounted bucky 126. The X-ray tube head rotational drive 270 (FIG. 3), which will be discussed further in greater detail, is controlled by system controller 510.

Thus, the tube crane 110, its associated drives 150 and 152, and the the X-ray tube head rotational drive 270, cooperate to allow the the system controller 510 to direct the X-ray tube head 112 to an arbitrary position on a reference plane parallel to the X-Z plane (within the range of travel provided by the mechanisms of the tube crane), and to point the emitted X-ray beam at an arbitrary angle along the reference plane. The transverse position of the reference plane is determined by the manually adjustable position of the tube crane transverse carriage 394, and normally is selected to be coincident with the longitudinal centerlines of table 116 and wall bucky 126. It is believed that providing three degrees of freedom for the position of the focal spot and the angular direction of the emitted X-ray beam, under control of the system controller 510, is sufficient for performing examinations using a variety of desirable radiographic, fluoroscopic, and tomographic imaging modes. However, a skilled artisan will appreciate that this embodiment may be easily modified to incorporate additional degrees of freedom if additional imaging modes are desired.

Figure 5:
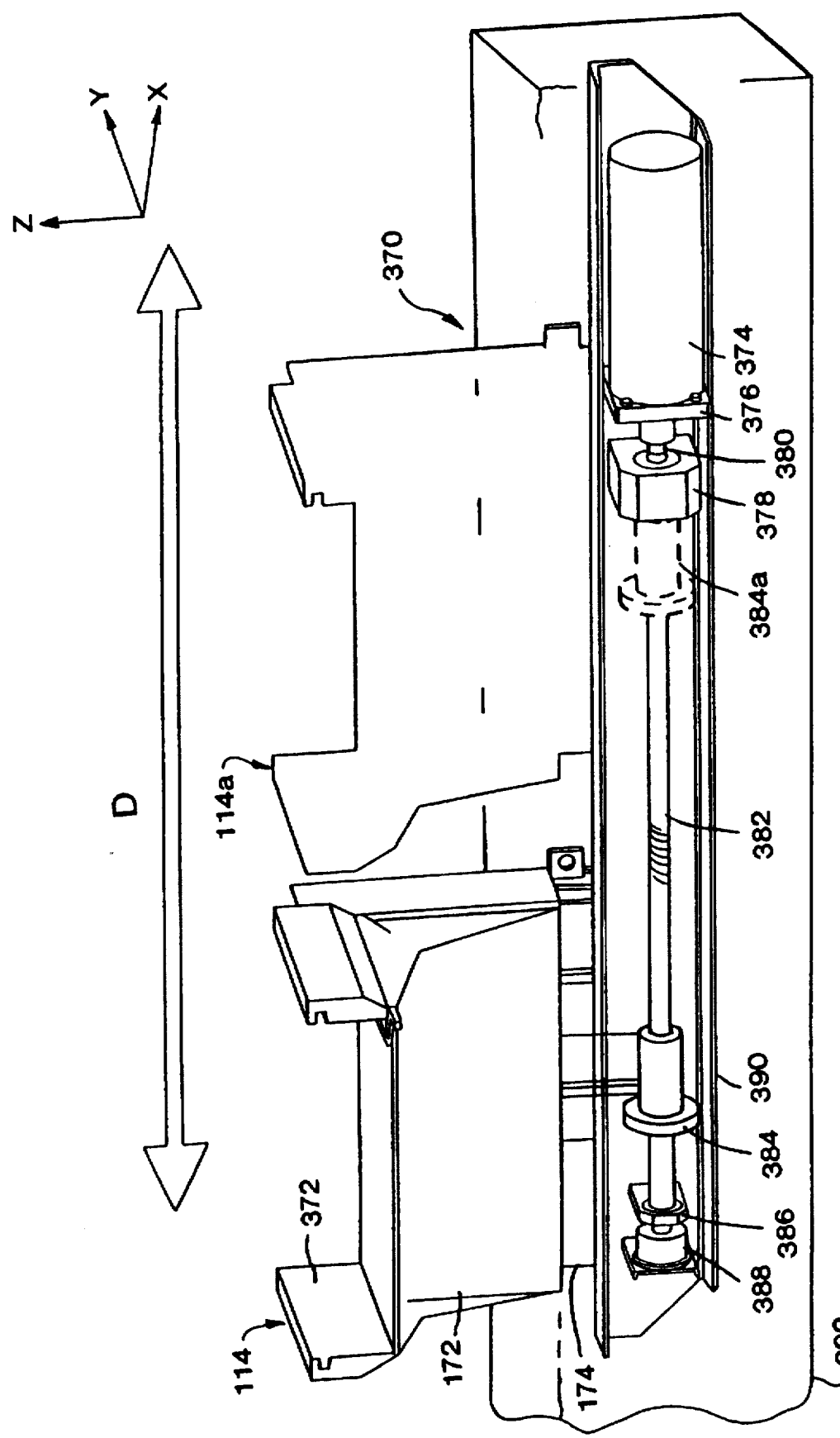
FIG. 5 is an oblique perspective view of a longitudinal drive system for controlling the longitudinal movement of a digital platform tower component of the inventive Universal Room of FIG. 1, in the direction shown by linear arrow D thereof.

A tiltable patient support table 116 is provided to support a patient (not shown) during examination. The table 116 preferably also supports a digital imaging platform 114 for conducting examinations using fluoroscopic and stepped techniques. The table 116 preferably comprises a base 186 for supporting the table and for housing a table tilt drive 450 (FIG. 7) The table tilt drive 450 simultaneously rotates the table about a transverse axis, as shown by arrow F, and translates the table. The translation is required to modify the effective center of rotation, thereby avoiding interference between the table and the floor. The base 184 preferably has a mounting and support plate 184 extending transversely to prevent the table from tipping due to the weight of the movable portion of the table, which is cantilevered from the base 184. Table 116 preferably further comprises a table top surface 176 movable in longitudinal and transverse directions as shown by arrows J and K by a 4-way drive system 560 (FIG. 5). The table top drive 560 is controlled by the system controller 510. The movable table top 176 allows a patient to be moved to a desired position for examination.

Table 116 preferably further comprises an imaging media cassette or "bucky" 128 disposed in a horizontal shaft 178 below and parallel to the table top surface 176. The bucky has an interior region 404 for receiving an appropriate imaging medium, such as a piece of radiographic film (not shown). The bucky 128 also has a radiographic grid (not shown) for attenuating scattered radiation approaching the imaging medium. The bucky 128 is movable longitudinally within shaft 178 by a table bucky drive 410 (FIG. 6) (discussed further in greater detail). Table bucky drive 410 is controlled by the system controller 510. The table 116 may have a control panel 180 to allow the operator to select the position of the table top 176 and the bucky 180.

A digital imaging platform 114 is provided to perform fluoroscopy, digital image acquisition, and related imaging operations. The digital imaging platform comprises a support tower 174 extending vertically from the table, a support bracket 172 attached to the support tower 174, an X-ray tube assembly 182 disposed below the table top surface 176 and mechanically coupled to the support tower 174, a digital platform control panel 168 attached to the bracket 172, a positioning control handle 170, and an image intensifier and camera module 166 attached to the support bracket and disposed above the table top surface 176. The X-ray tube 182 and image intensifier module 166 are preferably fixedly mechanically coupled and aligned so that radiation from the X-ray tube 182 is directed toward a radiation receiving portion of the image intensifier module 166. The image intensifier module 166 is provided to convert received radiation to representative electrical signals 488 for viewing on a monitor 486 or for further processing by other components (not shown).

The digital imaging platform 114 is preferably mechanically coupled to the table 116 using suitable bearing means (not shown) permitting longitudinal translation of the platform 114 with respect to the table 116, as shown by arrow D. An imaging platform longitudinal drive 370 (FIG. 5) is controlled by the control system 510 to direct the imaging platform to a longitudinal position selected by the operator or, in some imaging modes, by the control system. The control handle 170 preferably includes sensors (not shown) for sensing the direction of force applied to the handle by an operator indicating a desired direction of movement of the platform 114. Information obtained from the sensors is preferably communicated to the system controller 510, which produces control signals to longitudinal drive to move the platform 114 in the desired direction.

The inventive Universal Room 100 preferably further comprises a wall-mounted fixture 124 for supporting an additional imaging media cassette holder or bucky 126. The fixture 124 preferably comprises a vertical support member 190, and an imaging media cassette holder or "bucky" 126 mounted for vertical movement along the vertical support member 190, as shown by arrow H. The fixture 124 further comprises means 192 for sensing the vertical position of the bucky 126, and a cap member 194 disposed at the top of the vertical support 190 for securement to a support surface and for receiving electrical connections. The bucky 126 has an interior region (not shown) for receiving an appropriate imaging medium, such as a piece of radiographic film (not shown). The bucky 126 may have a radiographic grid (not shown) for attenuating scattered radiation approaching the imaging medium. The fixture 124 is preferably aligned with the reference plane containing the center line of the table 116. The fixture 124 may be secured to the floor 130 using a conventional mounting bracket 198 and suitable fasteners 202, such as bolts. The cap member 194 may be secured to the wall 132 using suitable conventional fasteners 196.

The position of bucky 126 may be manually controlled by the operator, but is not driven. However, the control system 510 receives an electrical signal 518 indicating the vertical position of the bucky 126 as sensed by sensor 192. A skilled artisan will appreciate that the preferred embodiment may be easily modified to drive wall mounted bucky 126 under control of control system 510 if necessary to accomplish a desired imaging mode.

A main control panel 120 interacts with control system 510 to allow the operator to select operating modes and other functional parameters of the inventive Universal Room 100. A monitor 486, which may be any suitable television or computer display, receives electrical signals 488 from the image intensifier module 466 or other processing components (not shown) and displays a corresponding image for use by the operator. An X-ray generator 118 provides electrical power for operating X-ray tubes 158 and 182. The X-ray generator converts 118 electrical power from a commercial AC power source to high-voltage DC at a selected voltage, for a selected duration, as instructed by control system 510. The X-ray generator also supplies power to heat the cathodes of the X-ray tubes 158, 182. The X-ray generator 118 preferably regulates the power supplied to the X-ray tube cathodes to achieve a desired tube operating current as instructed by the control system 510. A suitable X-ray generator 118 for use in this application is commercially available from Continental X-Ray Corporation, 2000 S. 25th Avenue, Broadview, Ill. 60153 (the assignee of the present application), under the name TM Series Generator. Other commercially available X-ray generators could also be used, by modifying them for compatible communication with control system 510. Although the monitor 486, main control panel 120, and X-ray generator 118 are shown adjacent table 116, they may be remotely located to avoid exposure of the operator to X-rays.

Figure 2:
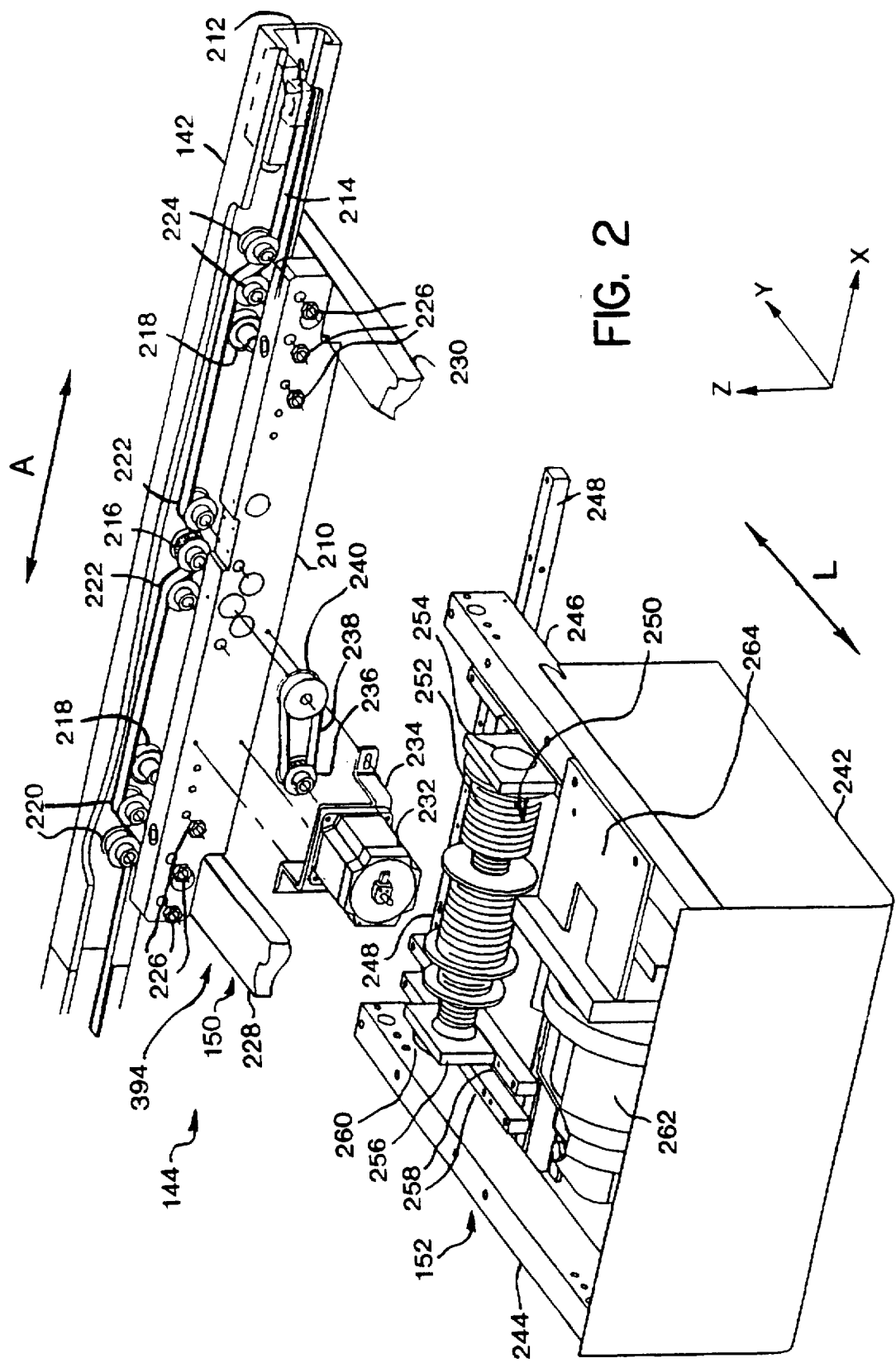
FIG. 2 is a partially exploded oblique perspective view of a longitudinal drive system for controlling the vertical movement of a tube crane component of the inventive Universal Room of FIG. 1, in the direction shown by linear arrow A thereof.
Figure 4:
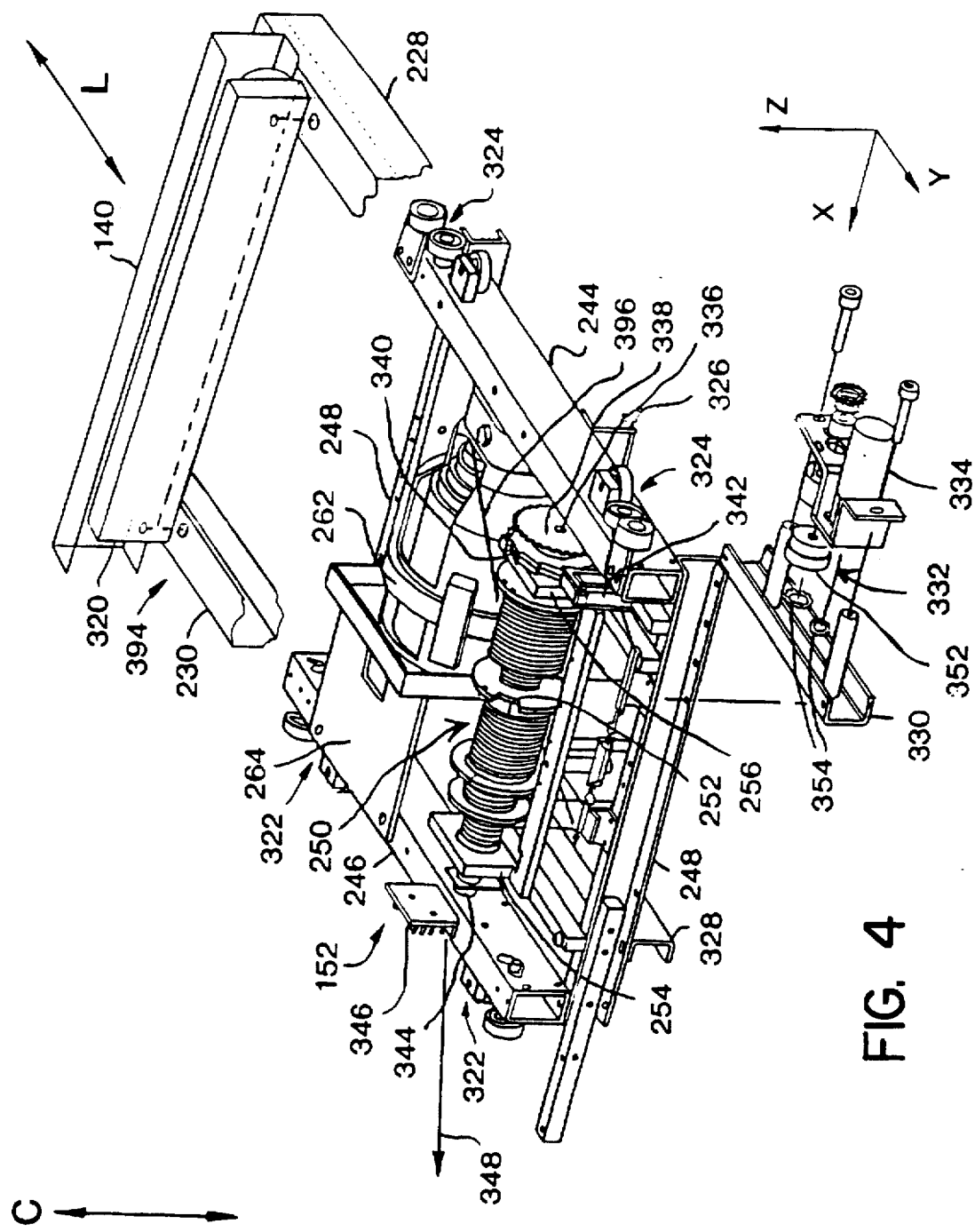
FIG. 4 is a partially exploded oblique perspective view of a vertical drive system for controlling the longitudinal movement of a tube crane component of the inventive Universal Room of FIG. 1, in the direction shown by linear arrow C thereof.

As best seen in FIGS. 1, 2, and 4, the tube crane assembly 110 preferably includes a bridge 144, a transverse carriage 394, a longitudinal drive 150, and a vertical drive 152. The longitudinal drive 150 controls the movement of the bridge 144, and the tube crane components supported thereby, in the longitudinal direction indicated by arrow A. The bridge 144 is supported by first and second longitudinal bearing assemblies 320 (FIG. 4) and 210 (FIG. 2) which travel longitudinally within rails 140 and 142, respectively. The tube crane assembly 110 and the X-ray tube head 112 have considerable mass and therefore, the rails 140, 142, fastening means 148, and supporting ceiling structure are preferably constructed to safely support the load presented by the tube crane and X-ray tube head.

The bridge 144 includes first and second support rails 228, 230 which are attached to and extend transversely between the longitudinal bearing assemblies 320 and 210. The transverse carriage 394 is supported by first and second transverse bearing assemblies 244 and 246 which travel transversely within the first and second transverse support rails 228, 230, respectively, as shown by arrow L. Bearings 324 and 322 provided on bearing assemblies 244 and 246, respectively, permit the transverse carriage 394 to travel transversely along the support rails 228, 230. The transverse carriage 394 includes additional structural members 248, 326 (FIG. 4) which are attached to, and extend longitudinally between, the first and second transverse bearings 244 and 246. A further support 328 member is attached to and extends transversely below longitudinal members 248 and 326. A cover 242 may be attached to the vertical carriage to obscure the mechanisms therein from view.

As best seen in FIG. 2, the longitudinal drive 150 preferably comprises a drive motor 232, a mounting bracket 234 for securing the motor 232 to longitudinal bearing 210 assembly, intermediate drive sprockets 236 and 240 coupled by a drive belt 238, a final drive sprocket 216 coupled to drive sprocket 240, and a final drive belt 214. The longitudinal bearing assembly 210 rides along the interior of the longitudinal support rail 142 on bearings 218. The final drive belt 214 extends along and inside of the longitudinal support rail 142 and is maintained under tension in a substantially fixed longitudinal position. The final drive belt 214 may constructed of any suitable webbed means, but is preferably a laminated, toothed belt of the type generally referred to as a "timing belt." The teeth of the final drive belt 214 engage the teeth of final drive sprocket 216, and guide pullies 222 maintain the belt 214 and sprocket 216 in secure engagement. The final drive belt 214 effectively forms as a flexible "rack" and the final drive sprocket 216 acts as a "pinion," so that rotation of the sprocket 216 causes relative motion between the longitudinal bearing assembly 210 and the support rail 142. Idler pullies 220 and 224 maintain the final drive belt 214 in a desired position and avoid interference between the belt 214 and bearings 218.

As best seen in FIGS. 2 and 4, the vertical drive 152 is preferably a cable drive mechanism. First and second bearing blocks 254, 256 provide support for a longitudinally extending axle 336. The axle 336 supports a pair of ganged cable spools 252, a drive sprocket 338, and a ratcheted brake wheel 248. Spools 252 are each preferably wound with suitable multifilament suspension cables 396 which extend through the telescoping tube assembly 154 (FIG. 1), and are attached to and support the X-ray tube head 112. Thus, the X-ray tube head 112 may be raised or lowered by winding or unwinding cable from the spools 252.

A drive motor assembly 332 including a drive motor 334 mounted on a support 330 is mechanically coupled through a clutch 352 and small drive sprockets 354 to the large drive sprocket 338. As a safety feature, the clutch is preferably adjusted to slip when the tension on the suspension cable 396 exceeds 20 pounds. The drive motor assembly 332 provides power to wind and unwind the spools 252. An electrically operated brake 342, which may be a solenoid or electromagnet, selectably engages the ratcheted brake wheel 248 to securely lock the wheel 248, axle 336, and spools 252 in a desired position. When set, the brake 342 prevents vertical movement of the X-ray tube head 112, because the fixed spools 252 prevent the release of any additional suspension cable. The brake 342 automatically releases when power is removed from the system, allowing the operator to manually move the X-ray tube head 112 to a desired position.

Preferably, a suitable sensor 344 provides a signal 348 to the control system 510 responsive to the angular displacement of axle 336, thereby indicating the position of the X-ray tube head 112. For example, the sensor 344 may be a multi-turn potentiometer mechanically coupled to to axle 336. An amplifier 346 may be used to convert the output of the potentiometer to an electrical signal 348 suitable for use by the control system 510.

The vertical drive 152 preferably also comprises a cable tensioner and main-spring assembly 262 which substantially counterbalances the weight of the X-ray tube head 112 and telescoping tube assembly 154. This counterbalancing significantly reduces the required capacity of the drive motor 334. The support cable 396 is is mechanically coupled to the main-spring assembly 262 using any suitable coupling. For example, the support cable 396 may be wound in tight frictional engagement about a drum (not shown) in the main spring assembly.

Figure 3:
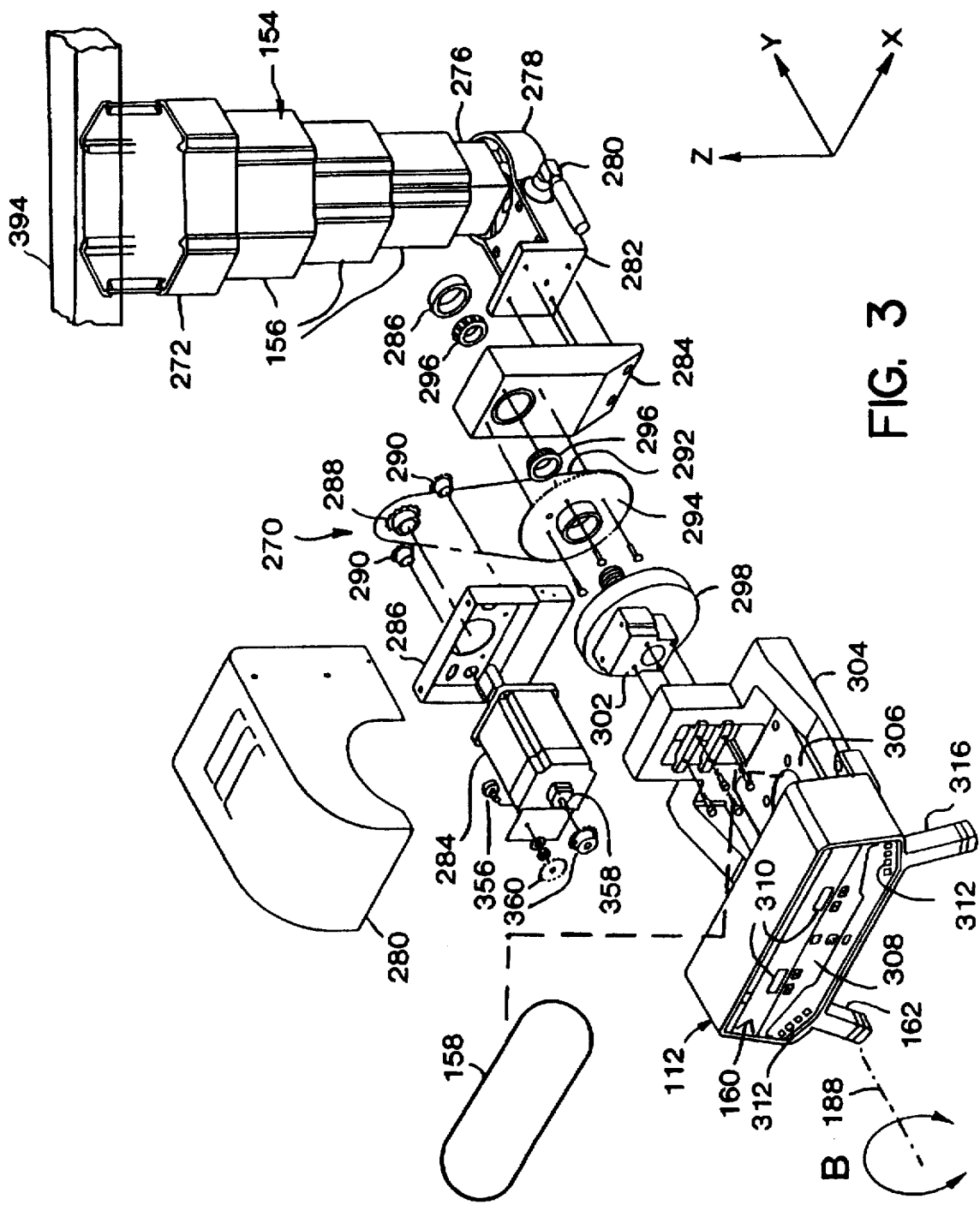
FIG. 3 is a partially exploded oblique perspective view of a rotational drive system for controlling the rotational movement of an X-ray tube head component of the inventive Universal Room of FIG. 1, in the direction shown by circular arrow B thereof.

FIG. 3 is a partially exploded view of an angulation drive system 270 for the X-ray tube head 112. The drive 270 controls rotational movement of the X-ray tube head 112 about an axis 188, as shown by circular arrow B. As best seen in FIGS. 1 and 3, the X-ray tube head is mechanically attached to and suspended by the telescoping tube assembly 154 of the tube crane 110. The telescoping tube assembly 154 has a upper base portion 272, which is secured to the transverse carriage 394, plurality of nested tubular structural members 156 having bearings to allow longitudinal slidable movement therebetween, and mounting block member 276 for attaching the X-ray tube head.

The X-ray tube head 112 comprises an X-ray tube mounting structure 304, a collimator mounting plate 306 attached to the tube mount 304, a control panel 160 attached to the tube mount 304, handles 162 and 316, and the angulation drive system 270 coupled to the tube mount 304. A releasable coupler 278 is preferably provided for mating the angulation drive system 270 to the mounting block member 276 of the telescoping tube assembly. A locking handle 280 may be manually operated to lock or unlock the coupler, allowing the X-ray tube head 112 to be conveniently attached to or released from the telescoping tube assembly 154 of the tube crane 110.

The coupler 278 has a flange 282 for mounting a bearing block 284. The bearing block 284 supports first and second bearings 296 and a retainer 286. The bearing block 284 also supports a drive sprocket 294 which is fixed with respect to the block 284, mounting coupler 298, which is rotatable with respect to the block. The mounting coupler 283 supports the tube mount 304, and a mounting plate 286 for drive motor 284. Thus, the mounting coupler 298, the tube mount 304, the control panel 160, and the drive motor 284, form a rotational unit which rotates with respect to the fixed bearing block 284.

The drive motor 284 is attached to mounting plate 285 using any suitable fastening means. A drive sprocket 288 is attached to the output shaft of the drive motor 384. A drive chain, drive belt, or any suitable webbed means 292 provides an operative mechanical coupling between drive sprocket 288 and fixed drive sprocket 294. Idler sprockets 290 maintain tension on the drive chain or drive belt. In operation, rotation of the motor 284 effectively drives the rotational unit around the drive sprocket 294. Motor 284 may be any suitable motor which is compatible with closed-loop positioning control, such as a stepping motor or a servo-motor of conventional design. The angulation drive preferably comprises suitable means for providing feedback to the control system 510 of the position and motion of the X-ray tube head 112. For example, an optical encoder 358, and a potentiometer 356, driven by a suitable coupling, such as gears 360, preferably produce electrical signals 546 (FIG. 15) for use by the control system 510. A housing 280 is provided to cover the components of the angulation drive 270.

The universal control panel 160 is provided on the X-ray tube head 112 to allow the operator to control many functions of the inventive Universal Room 100. For example, switches 312 may be used to control the motion of the tube crane longitudinal and vertical drives and the X-ray tube head angulation drive. Switches 308 may be used to select the operating mode of the system, and other system parameters. Switches and displays 310 may be used to control X-ray tube exposure parameters (referred to as "technique") such as tube voltage and tube current.

FIG. 5 is a perspective view of a longitudinal drive system 370 for controlling the longitudinal movement of the digital imaging platform 114 along the direction of arrow D. The longitudinal drive system preferably comprises a longitudinally extending support rail or track 390 in a housing 392. A vertically extending tower portion 174 of the digital imaging platform 114 is mounted via suitable bearings (not shown) for longitudinal travel along track 390.

A drive motor 374 is attached to track 390 by a suitable mounting block 375. First and second bearing blocks 378 and 386 are attached to the track 390 near opposite ends thereof, and support a lead screw 382 extending parallel to the track. The lead screw 382 is mechanically coupled to the motor output shaft 380. A ball screw follower 390 assembly is coupled to the lead screw 382. The vertically-extending tower portion 174 of the digital imaging platform 114 is mechanically attached to the ball screw follower 390. Thus, by virtue of its attachment to ball screw follower 390, the digital imaging platform 114 is driven longitudinally by rotation of the motor 374 among various positions. The ball screw follower and digital imaging platform are shown in a first position, denoted by reference numbers 390 and 114, and a second position, denoted by reference numbers 390a and 114b.

Motor 374 may be any suitable motor which is compatible with closed-loop positioning control, such as a stepper motor or a servo-motor of conventional design. The digital platform longitudinal drive preferably comprises suitable means for providing feedback to the control system 510 of the position and motion of the platform. For example, a potentiometer 388 may be coupled to the lead screw 382 to produce an electrical signal representing the platform position for use by the control system 510.

A vertical drive system (not shown) may be provided to control the vertical position of the digital imagine platform 114. The vertical drive may be constructed using known techniques and may employ any suitable commercially available drive subsystem.

Figure 6:
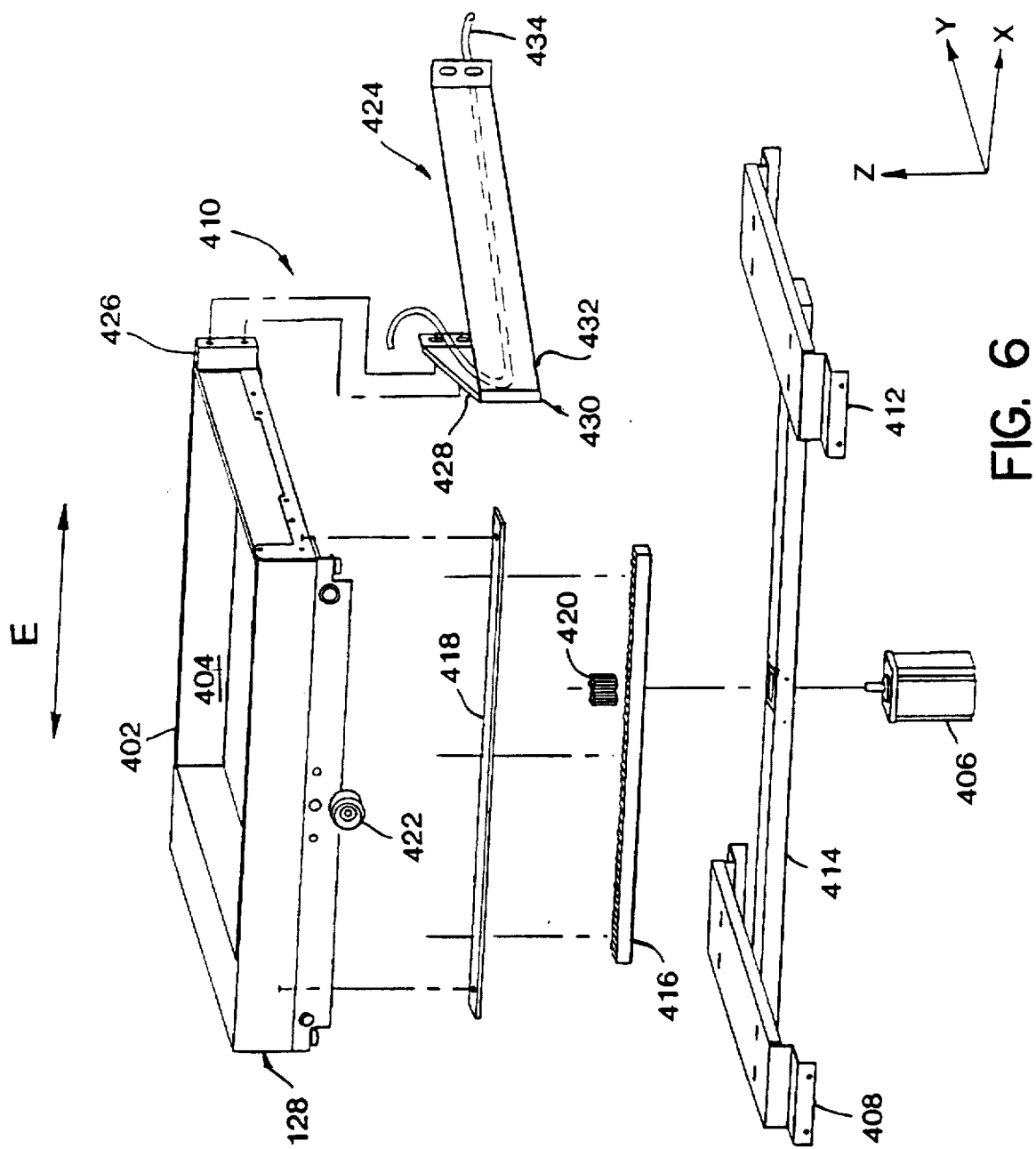
FIG. 6 is a partially exploded oblique perspective view of a longitudinal drive system for controlling the longitudinal movement of a patient table imaging cassette ("bucky") component of the inventive Universal Room of FIG. 1, in the direction shown by linear arrow E thereof.

FIG. 6 is a partially exploded oblique perspective view of a longitudinal drive system 410 for controlling the patient table ("bucky") 128 in the direction shown by linear arrow E. As best seen in FIG. 1, the table bucky 128 travels in a longitudinal shaft 178 disposed below the movable table top surface. The table bucky 128 comprises a frame structure 402 forming a region 404 for receiving a cassette (not shown) containing any suitable radiographic imaging medium, such as X-ray film. The bucky 128 travels on a bearing or roller 422 along at least one longitudinal rail or track (not shown) disposed in the shaft 178.

The table bucky 128 preferably further comprises a longitudinal gear rack mounting plate 418 attached to the bottom of the bucky, and a longitudinally extending gear rack 416 attached to the mounting plate 418. A drive motor support structure is disposed below the bucky travel shaft 178 and comprises side brackets 408 and 412, and a longitudinal motor mounting bracket 414 extending between the side brackets.

The motor 406 is attached to the longitudinal motor mounting bracket 414 at a suitable location between the side brackets 408, 412, such as the midpoint of bracket 414. Motor 406 may be any suitable motor which is compatible with closed-loop positioning control, such as a stepping motor or a servo-motor of conventional design. An aperture in the bracket 414 allows the motor output shaft to extend upward toward the bucky 128. A pinion gear 420 mounted on the motor output shaft engages the rack 420 so that rotation of the motor 406 causes longitudinal movement of the rack 420 and the bucky 128 attached thereto.

Figure 7:
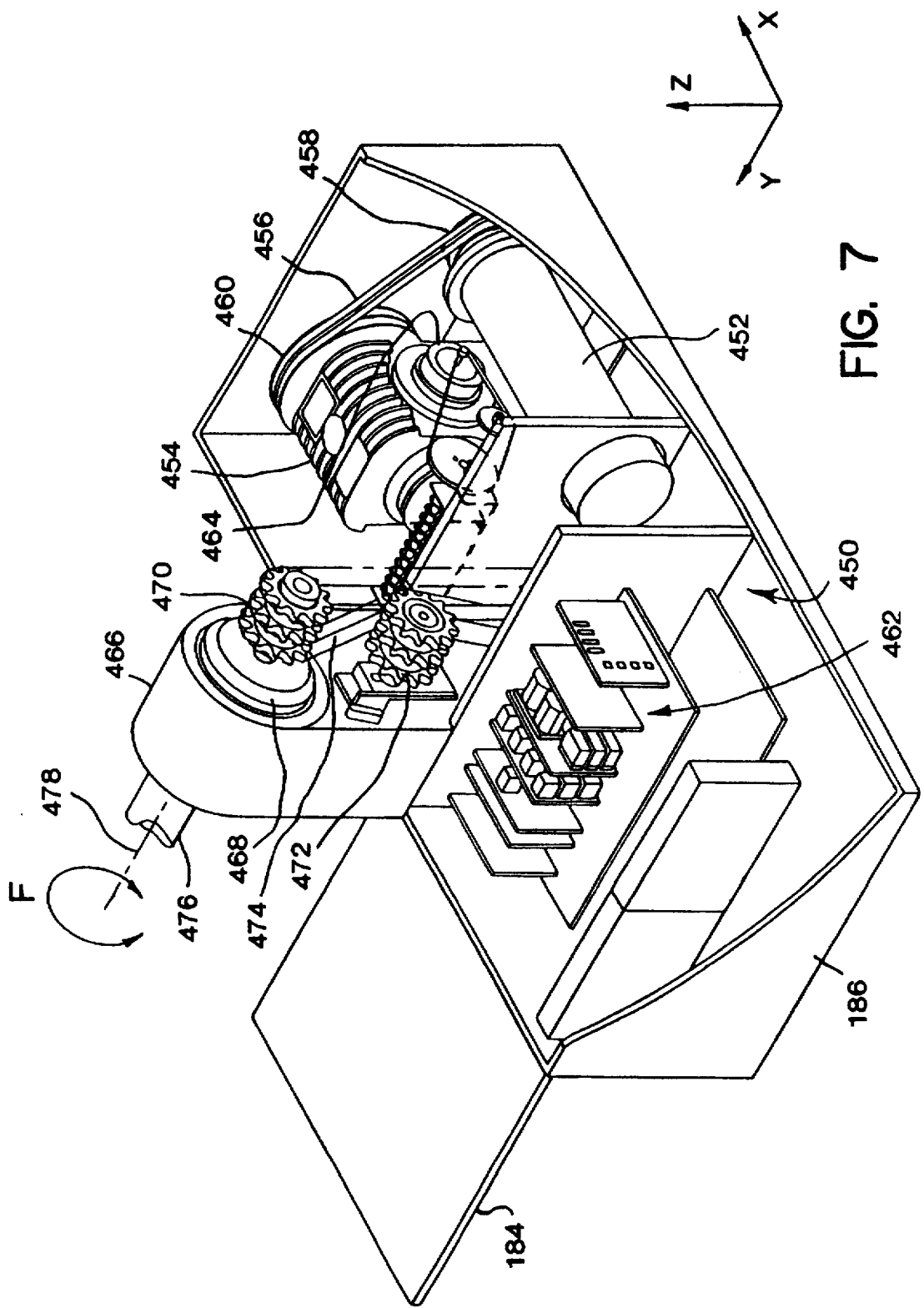
FIG. 7 is an oblique perspective view of a rotational (tilt) drive system for controlling the tilt movement of a patient support table component of the inventive Universal Room of FIG. 1, in the direction shown by circular arrow F thereof.

FIG. 7 is an oblique perspective view of a rotational drive system 450 for controlling the tilt movement of the patient support table 116, about an axis 478 in the direction shown by circular arrow F. The rotational table angulation drive 450 is housed in a base portion 186 of the table 116. The drive comprises a drive motor 452, with suitable drive electronics 462, a gear reducer 454, a bearing support 466, and an output shaft 476. Drive motor 452 and gear reducer 454 may be any suitable compatible motor and gear reducer having sufficient capacity, of which a large variety of appropriate products are commercially available. The output shaft 476 and bearing support 466 must bear the weight of the table 116, and therefore, the output shaft 476 is mounted for rotation on a high-capacity bearing 468, and the gear reducer 454 is preferably sized for adequate performance in conjunction with the load presented by the table 116.

A set of flexible drive means 456, which may be any suitable belt, chain, or webbed means, such as standard drive belts, couples power from a set of drive pulleys 458 mounted on the motor output shaft to drive pulleys 460 mounted on the input shaft of gear reducer 454. Another set of flexible drive means 474, which may be any suitable belt, chain, or webbed means, such as multiple-link drive chains, couples power from a set of drive pulleys (not shown) mounted on the gear reducer output shaft to a set of drive pulleys 470 mounted on the rotation drive output shaft 476. A set of idler pulleys 472 maintains suitable tension on flexible drive means 474. Preferably, drive position sensing means 464 is mechanically coupled to the output of the gear reducer 454 to provide an electrical signal 546 representing the table position for use by control system 510. The position sensing means 464 may be any suitable sensor, such as a potentiometer.

FIG. 15a is a general block diagram of a suitable control system 510 for use in coordinating the electrical and mechanical components of the inventive Universal Room 100 to perform a variety of useful medical imaging examinations. Several different types of interconnections are provided between the components of control system 510 of FIG. 15a. The legends "RS-232" and "RS-422" generally denote point-to-point serial data links which employ a standardized electrical line discipline. The legend "CAN Bus" denotes a serial data link among several interconnected components. The data is carried over a two-wire party line bus which may support a large plurality of independently addressed devices. Although four separate CAN bus links 516, 524, 526, and 540 are shown in the drawings, those links may be provided over as few as one, or as many as four, physical CAN busses, depending on traffic requirements. It is believed that satisfactory operation of the control system 510 may be obtained using two physical CAN busses. The electrical line discipline and message protocol of the CAN bus is described in the publication "CAN Bus Network" from Philips Semiconductor, Microcontroller Products Division. The legend "I/O Port" generally denotes non-serial signals which may be analog or digital.

As best seen in FIG. 15a, the control system 510 comprises a universal control panel 160, a tomography control module 568, a radiographic/fluoroscopic control module 566, an X-ray generator control module 120, a digital platform control module 554, and a multi-axis motion controller 512.

The universal control panel 160 is located on the X-ray tube head 112, and allows the operator to select, inter alia, the system's examination mode, and certain operating parameters for radiographic and tomographic exposures. The universal control panel 160 communicates with the tomography control module 568 via a CAN bus link 526 and with the radiographic/fluoroscopic control module 566 via RS-232 link 530.

The tomography control module 568 operates when the Universal Room 100 is performing a tomographic examination, and also operates any other time the overhead tube crane 110 is used. The tomography control module 568 issues requests to the radiographic/fluoroscopic control module 566 and the multi-axis motion controller 512 to drive the tube crane 110, X-ray tube head 112, and table bucky 128 in opposite directions about a fulcrum located on the desired tomographic imaging plane of the patient.

The digital platform control 554 communicates with digital platform 114 and table 116 via CAN bus 540, and with the digital platform display and control panel 168 via I/O ports 542. Those components, in turn, communicate with the table angulation drive 558 and the table-top surface four-way drive 560 via I/O ports 536 and 538. The radiographic/fluoroscopic control module 566 communicates with the universal control panel 160 via RS-232 link 530, the X-ray generator control 120 via RS-232 link 532, the digital platform control 554 via a CAN bus link 524, and the multi-axis controller 512 via can bus links 514 and 516.

In addition, both the multi-axis motion controller 512 and the radiographic/fluoroscopic control module 566 communicate with the table angulation drive 558 via I/O ports 522, the table top four-way drive 560 via I/O ports 520, the wall bucky position sensor 586 via I/O ports 518, the table bucky drive 572, the X-ray tube angulation drive 576, and the tube crane drives 578 and 580 via a CAN bus link 516. In most imaging modes, the radiographic/fluoroscopic control module 566 transmits requests to the multi-access motion controller 512 to control in real time the movement of each driven component required to perform the examination. The multi-axis motion controller 512 is capable of simultaneous real-time control of motion along up to four axes. Although the multi-axis motion controller 512 can communicate with a large plurality of client devices, none of the examination modes in which the inventive Universal Room 100 is intended to operate require simultaneous motion in more than four axes. However, the multi-axis motion controller 512 may be expanded to simultaneously control additional axes if new imaging modes so require.

The multi-axis motion controller 512 may be any appropriate real-time motion controller having sufficient throughput and compatible facilities for communicating with the drive systems and with the other control components of the control system 510. Any suitable commercially available motion controller capable of controlling simultaneously movements along at least four axes may be used. The tomography control module 568, the RF control module 566, the X-ray generator control 120, and the digital platform control 554 may be any implemented using any suitable control systems of sufficient computing and I/O capacity to control and interface with the required real-world devices. For example, each of these controllers may be constructed using conventional microprocessor and interface technology as is known in the art. Off the shelf general-purpose microcomputer-based control products may be used to implement these controllers, or each controller may be constructed by selecting only those facilities required to achieve the respective control functions.

Advantageously, the aforementioned versatile mechanical, electrical, and control components allow the inventive Universal Room 100 to provide a variety of useful medical imaging examination modes, which may be selected by the operator using the universal control panel 160. FIGS. 8–14 show the mechanical configuration of the inventive Universal Room 100 in each of several examination modes. FIGS. 15b–15f are diagrams of control system 510 in which those portions of the control system which are required to achieve particular examination modes are highlighted for clarity.

Figure 8:
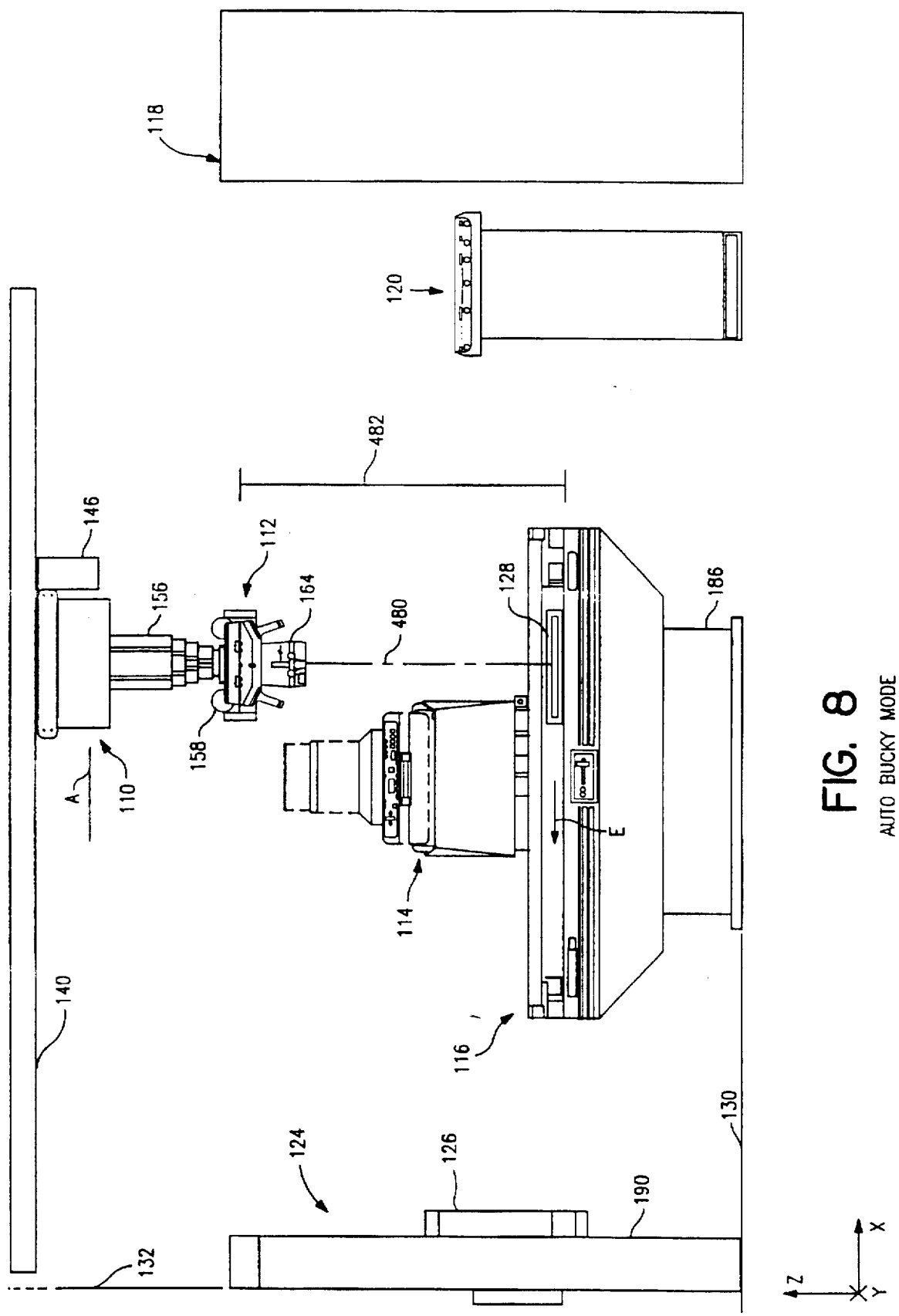
FIG. 8 is a side elevation view of the inventive Universal Room of FIG. 1, showing the coordinated movement of the tube crane and patient table imaging cassette components thereof, when the Universal Room is operating in an exemplary "auto-bucky" mode.

As best seen in FIGS. 8 and 15b, the inventive Universal Room 100 provides an "auto-bucky" mode. This is another radiographic imaging mode in which the crane-mounted X-ray tube head 112 is used to expose radiographic media in the table bucky 128. In this mode, the table 116 is tilted to occupy a horizontal position. The control system 510 directs the tube crane 110 and the X-ray tube head 112 to point toward the table bucky, as shown by X-ray beam projection 480. The universal control panel 160, radiographic/ fluoroscopic control module 566, and the multi-axis motion controller 512 cooperate to observe the longitudinal position of the tube crane and direct the table bucky 574 to follow the tube crane accordingly.

Figure 9:
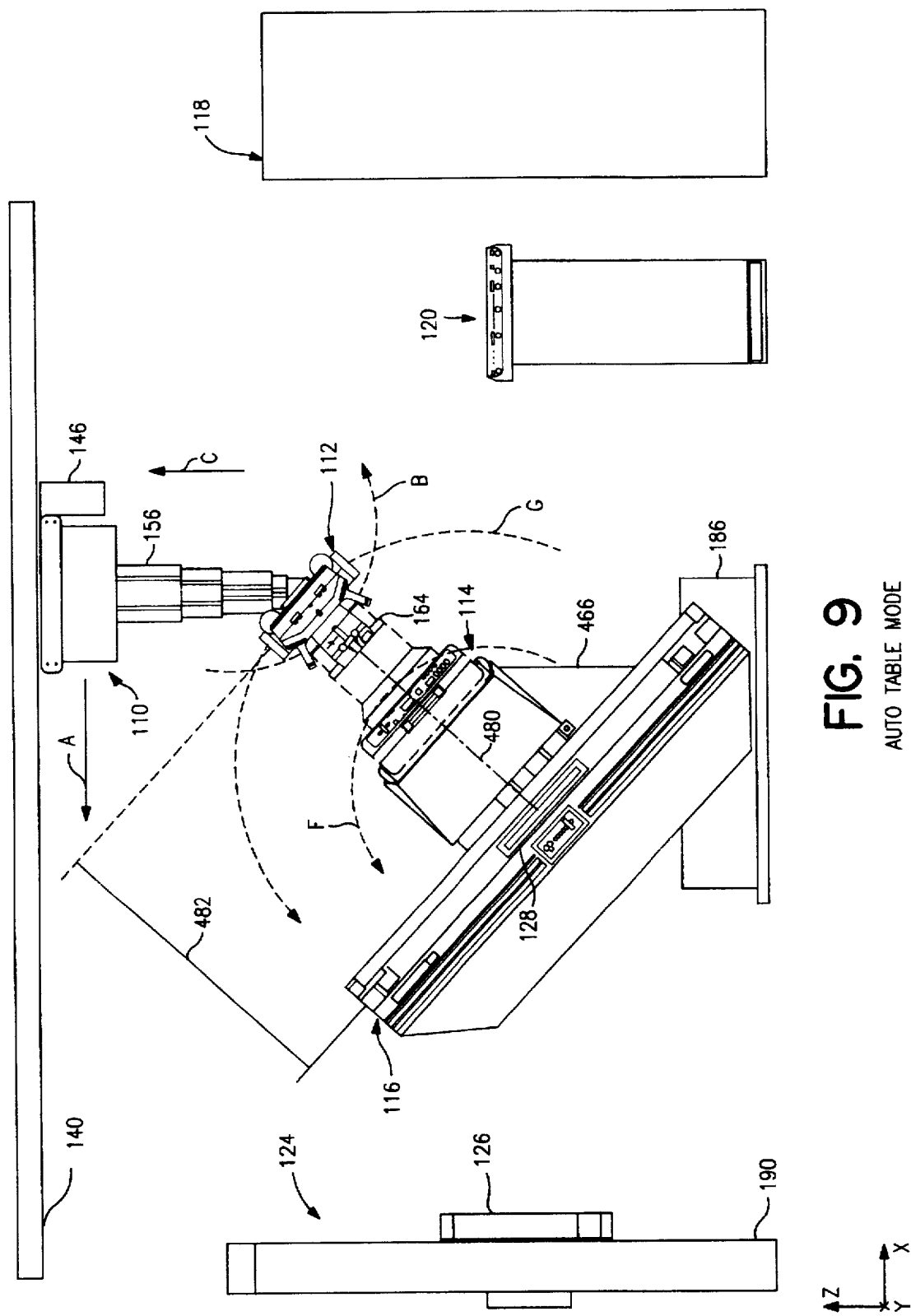
FIG. 9 is a side elevation view of the inventive Universal Room of FIG. 1, showing the coordinated movement of the tube crane, X-ray tube head, patient table, and imaging cassette components thereof, when the Universal Room is operating in an exemplary "auto-table" mode.
Figure 15C:
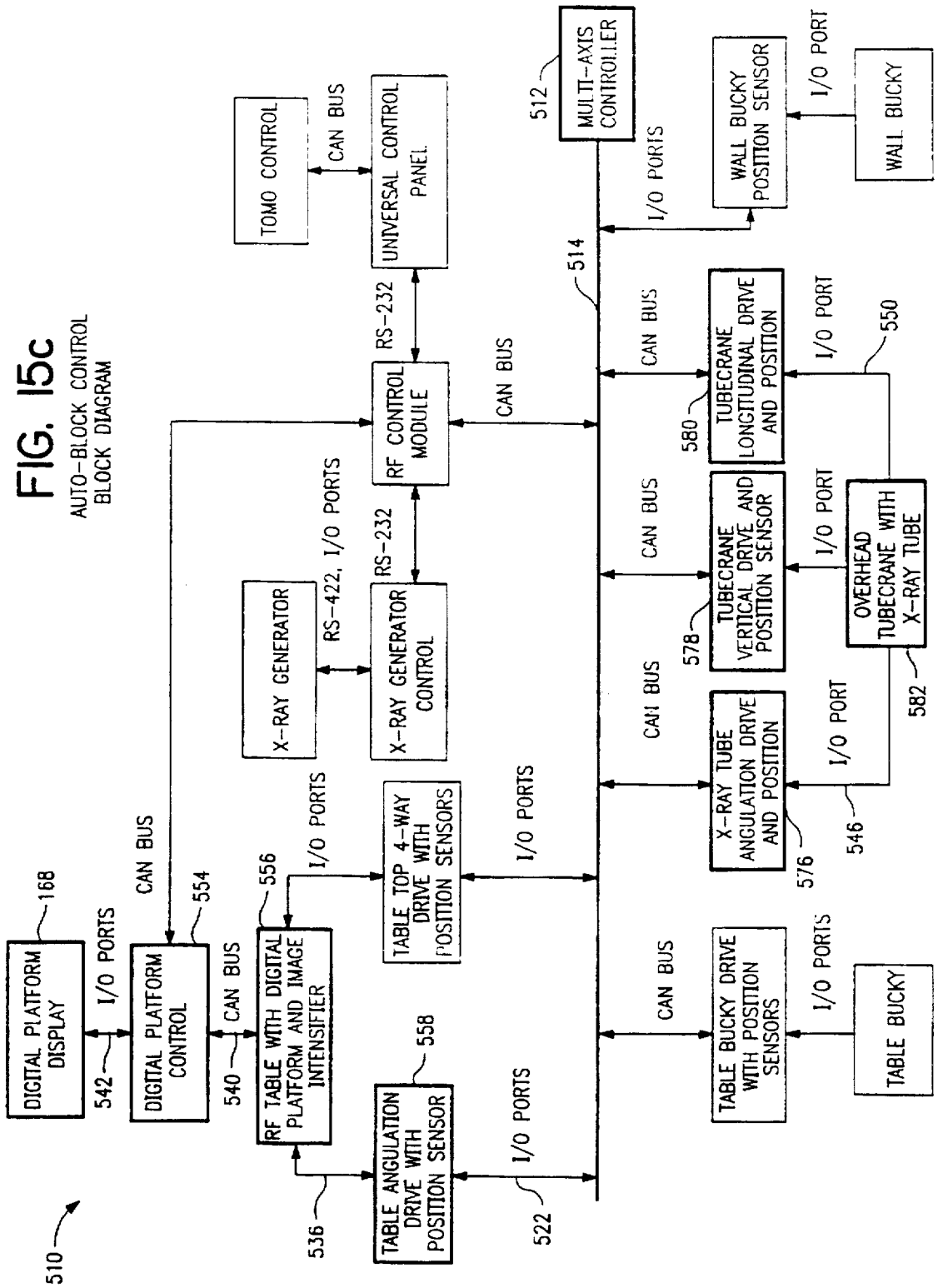
FIG. 15c is a block diagram of the exemplary control system of FIG. 15a for use in conjunction with the inventive Universal Room of FIG. 1, in which the control components used in providing real-time control for the "auto-table" and "auto-table/wall" modes of FIGS. 9–10 are emphasized for clarity.
Figure 16:
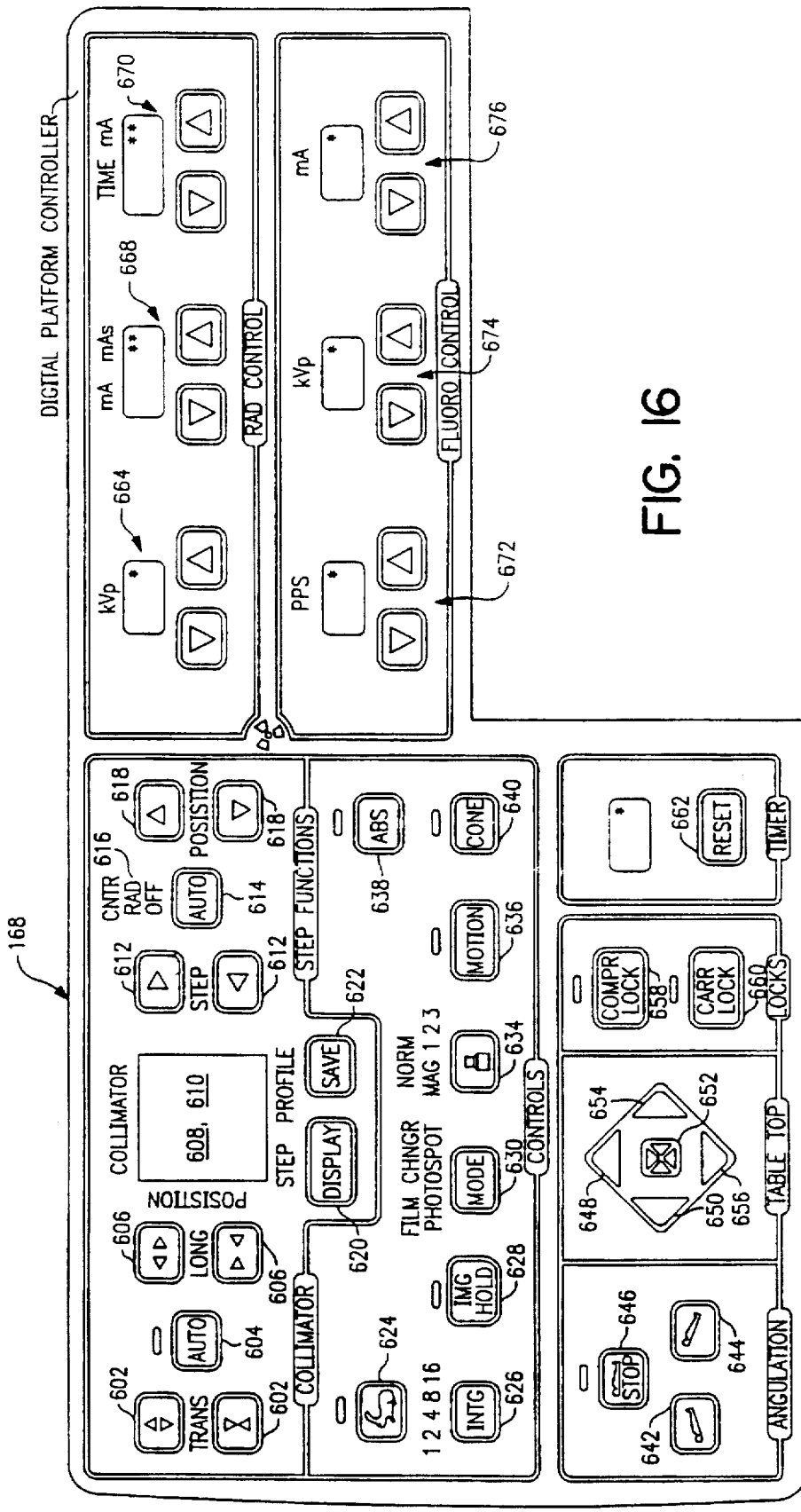
FIG. 16 is a diagram showing an exemplary control panel for use in controlling the operation of the digital imaging platform component of the inventive Universal Room.

As best seen in FIGS. 9 and 15c, the inventive Universal Room 100 provides an "auto-table" examination mode. This is a radiographic imaging mode in which the crane-mounted X-ray tube head 112 is used to expose radiographic media in the table bucky 128. In this mode, the table 116 occupies an angular position displaced from the horizontal. The control system 510 directs the tube crane 110 and the X-ray tube head 112 to point toward the table bucky, as shown by X-ray beam projection 480. The digital platform control 554, the table 116 and digital imaging platform 114, the table angulation drive 558, the X-ray tube angulation drive 576, the tube crane vertical and longitudinal drives 578, 589, and the multi-axis motion controller 512 cooperate to position the tube crane 110 and X-ray tube head 112 such that the X-ray beam is normal to the bucky and a selected source-image-distance SID is maintained. The desired SID is determined by the focal length of the radiographic grid of the bucky 126. For a typical bucky, the focal length is approximately 40 inches.

Figure 10:
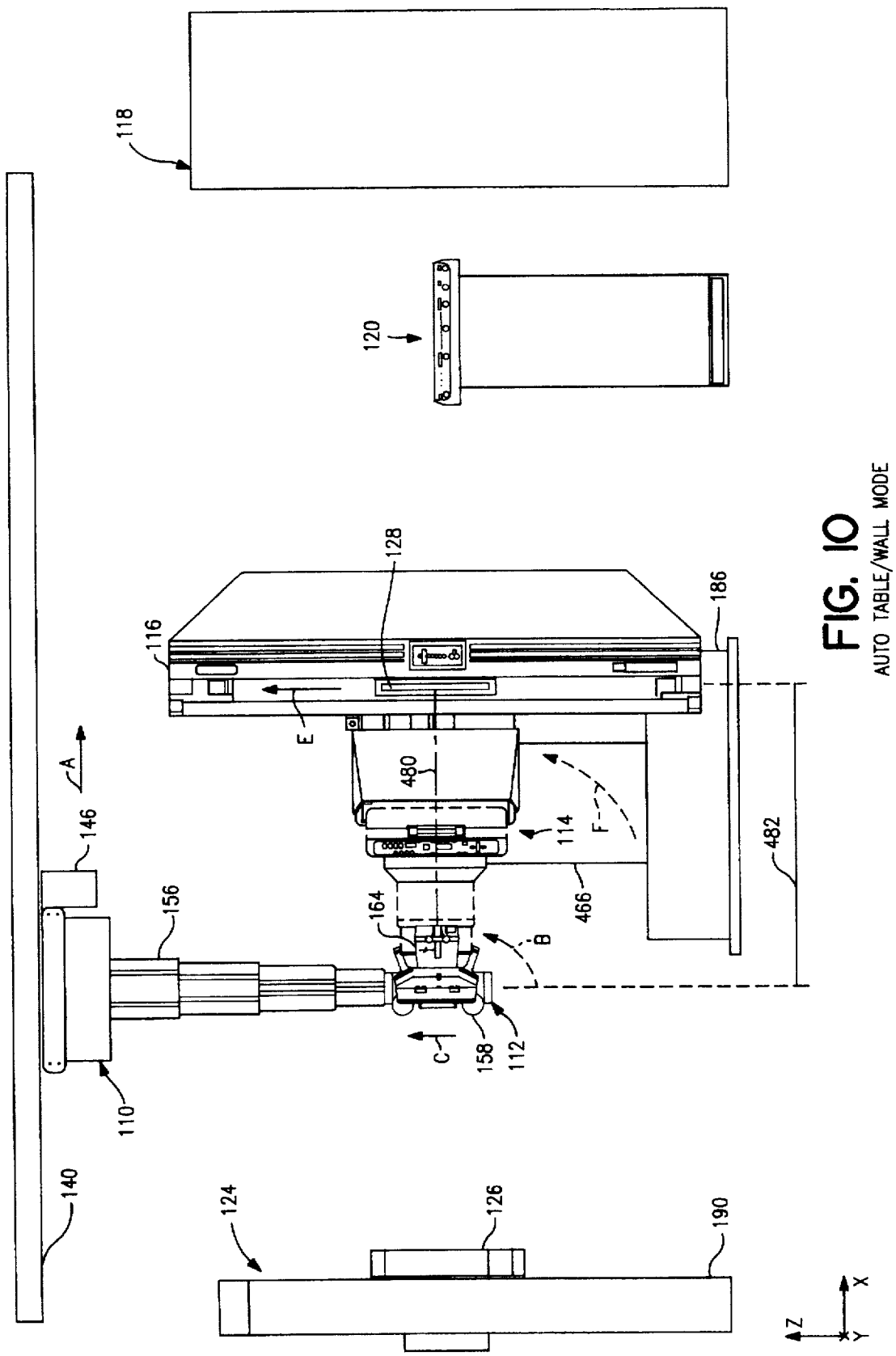
FIG. 10 is a side elevation view of the inventive Universal Room of FIG. 1, showing the coordinated movement of the tube crane, X-ray tube head, and patient table imaging cassette ("bucky") components thereof, when the Universal Room is operating in an exemplary "auto-table/wall" mode.

As best seen in FIGS. 10 and 15c, the inventive Universal Room 100 provides an "auto-table/wall" examination mode. This is a radiographic imaging mode in which the crane-mounted X-ray tube head 112 is used to expose radiographic media in the table bucky 128. In this mode, the table 116 is placed in the vertical position. The control system 510 directs the tube crane 110 and the X-ray tube head 112 to point toward the table bucky, as shown by X-ray beam projection 480. The digital platform control 554, the table 116 and digital imaging platform 114, the tube crane vertical and longitudinal drives 578, 589, the tube head 112 angulation drive, and the multi-axis motion controller 512 cooperate to cause the table bucky to follow the position of the tube crane 110 (within the limits of its travel) while maintaining the X-ray beam normal to the bucky, and maintaining a desired SID.

Figure 11:
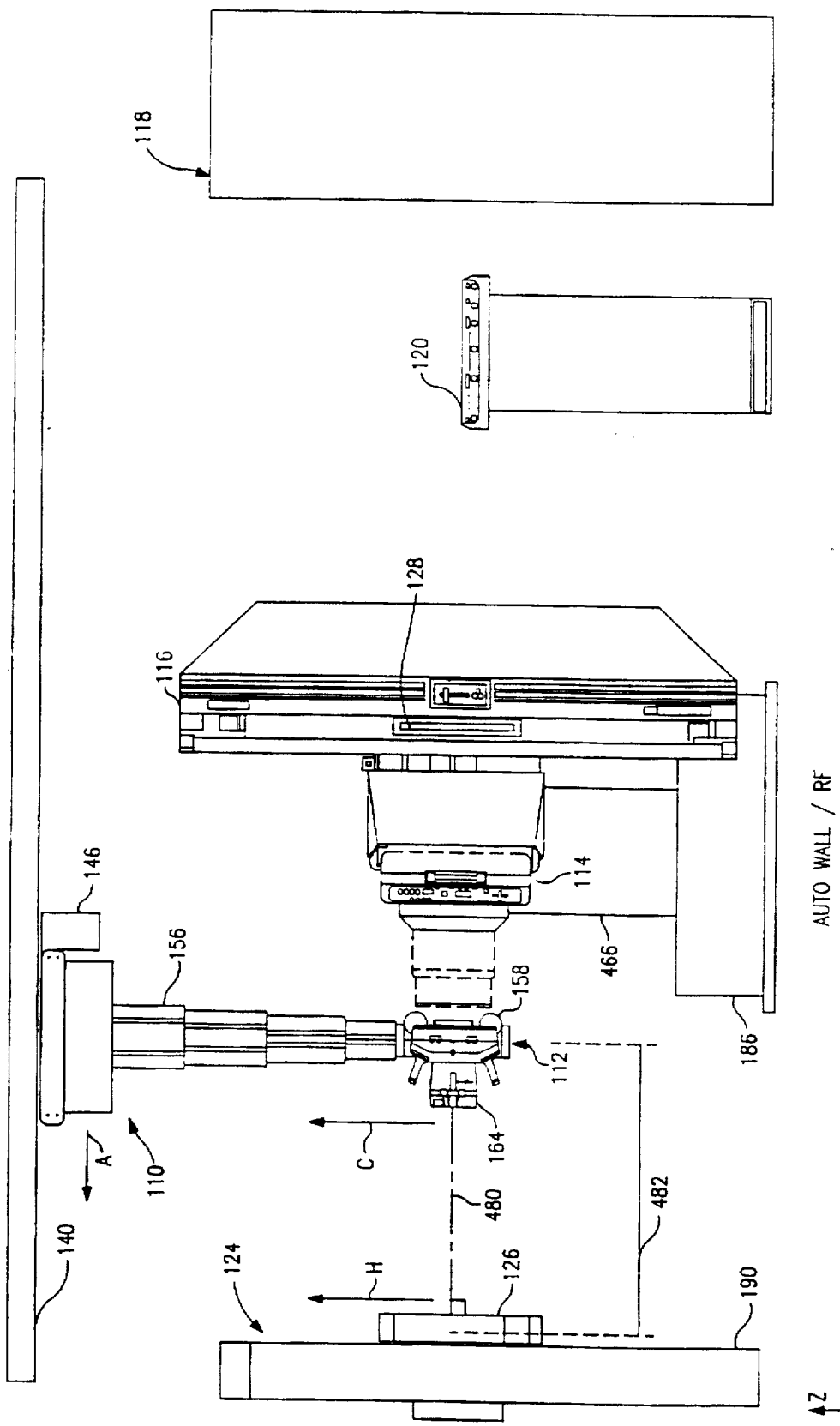
FIG. 11 is a side elevation view of the inventive Universal Room of FIG. 1, showing the coordinated movement of the tube crane and wall-mounted imaging cassette ("bucky") components thereof, when the Universal Room is operating in an exemplary "auto-wall" mode.
Figure 15D:
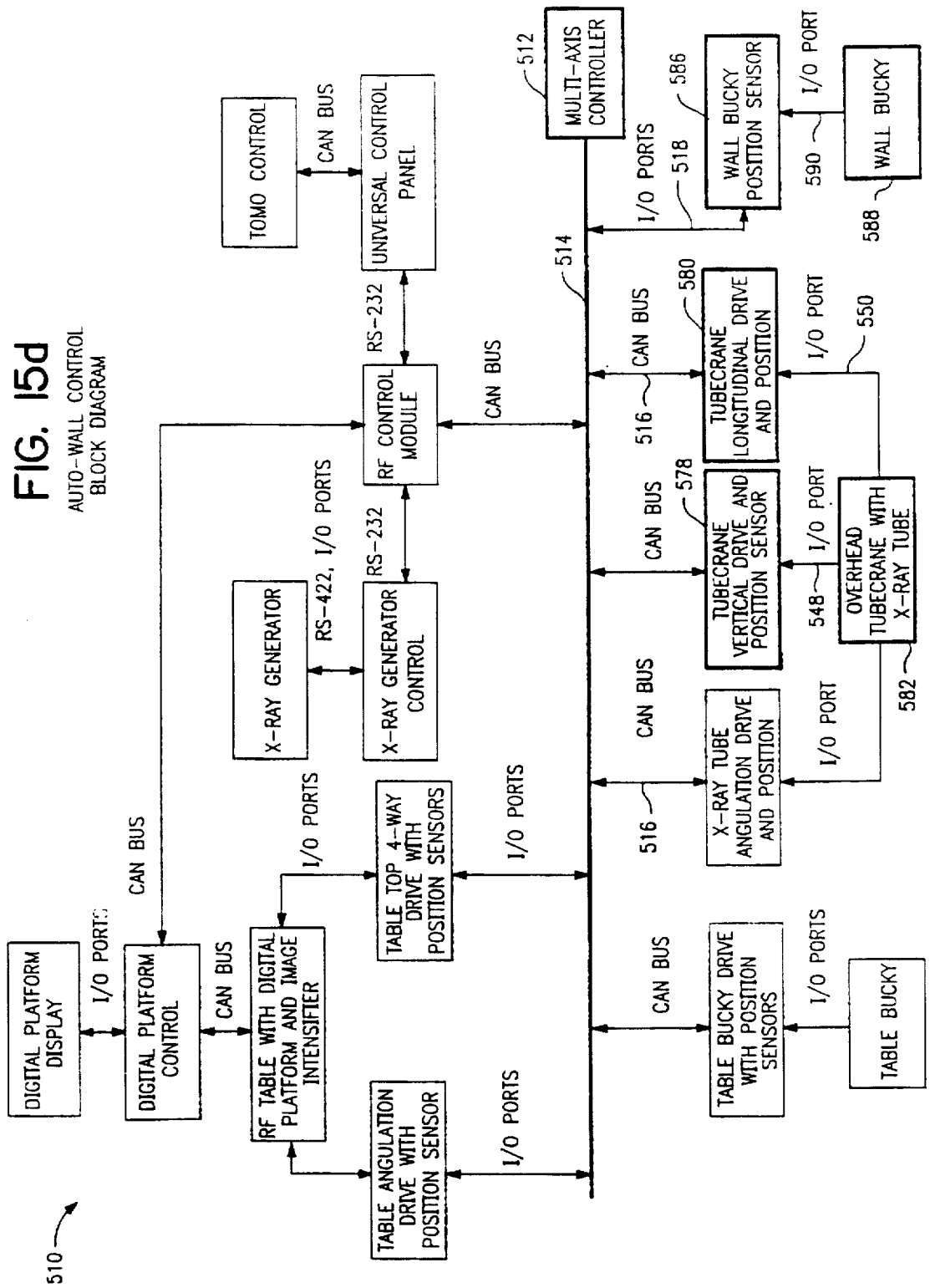
FIG. 15d is a block diagram of the exemplary control system of FIG. 15a for use in conjunction with the inventive Universal Room of FIG. 1, in which the control components used in providing real-time control for the "auto-wall" mode of FIG. 11 are emphasized for clarity.

As best seen in FIGS. 11 and 15d, the inventive Universal Room 100 provides an "auto-wall" examination mode. This is a radiographic examination mode in which the crane-mounted X-ray tube head 112 is used to direct an X-ray beam toward the wall-mounted bucky 126. The tomography control module must be set to the "wall" mode. Note that the wall-mounted bucky 126 is not driven, but its position is sensed and reported to control system 510. The wall bucky position sensor 586, tube crane vertical and longitudinal drives 578, and 580, and the multi-axis motion controller 512, cooperate to position the X-ray tube head 112 such that it follows the position of the wall-mounted bucky 126, while maintaining the X-ray beam direction normal to the bucky, and preserving the desired SID.

Figure 12:
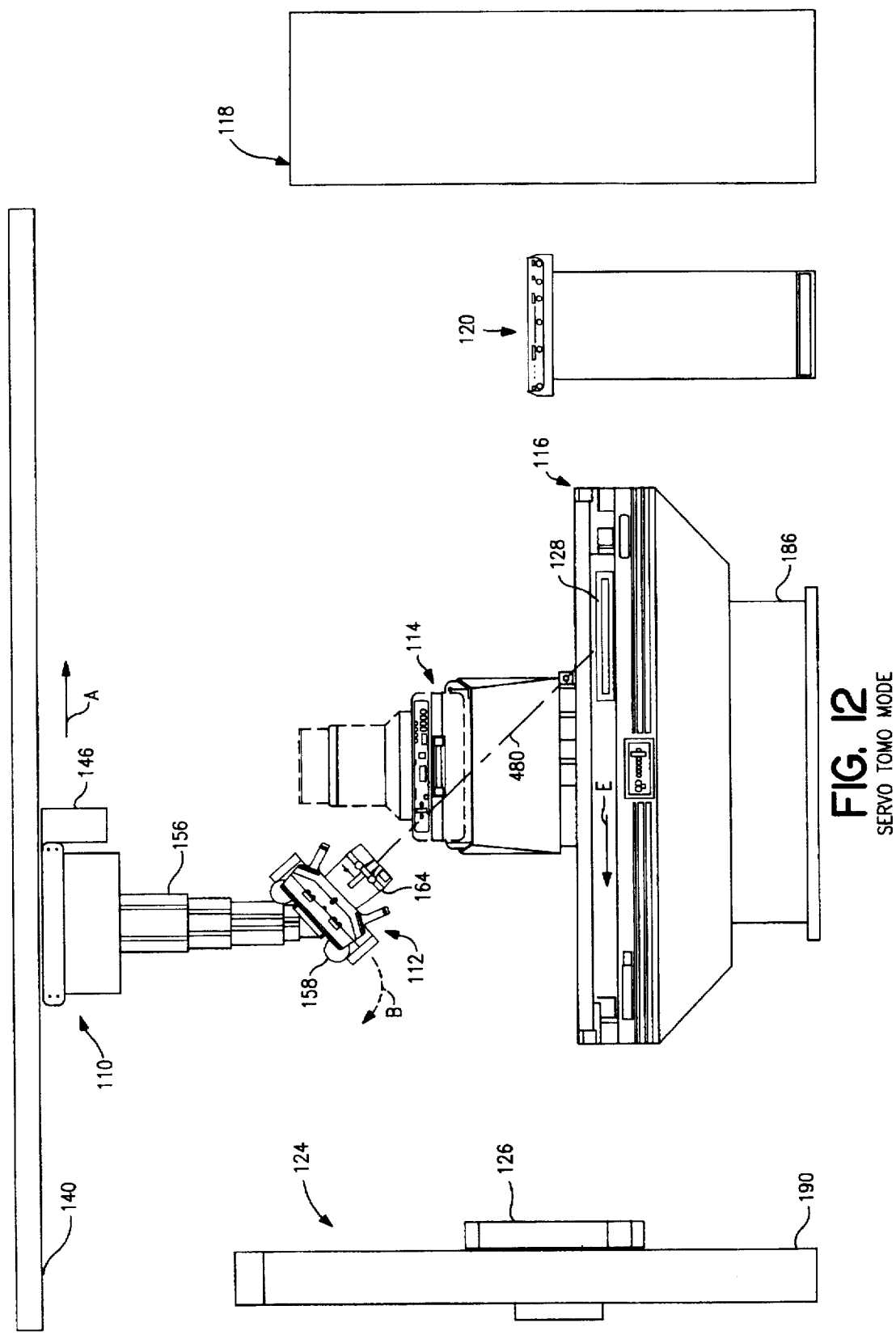
FIG. 12 is a side elevation view of the inventive Universal Room of FIG. 1, showing the coordinated movement of the tube crane, X-ray tube head, and a patient table imaging cassette ("bucky") components thereof, when the Universal Room is operating in an exemplary "servo-tomo" mode.
Figure 15E:
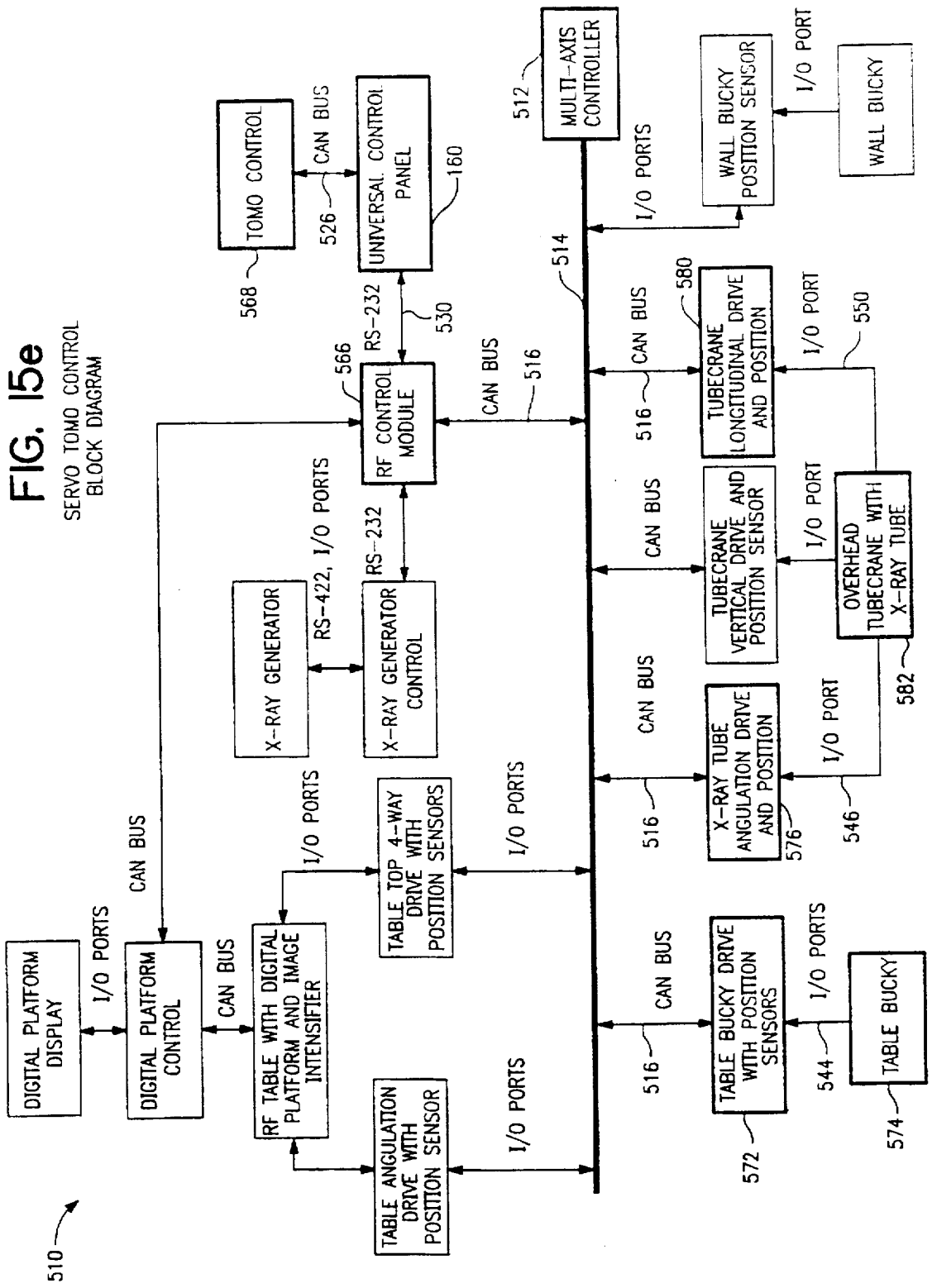
FIG. 15e is a block diagram of the exemplary control system of FIG. 15a for use in conjunction with the inventive Universal Room of FIG. 1, in which the control components used in providing real-time control for the "servo-tomo" mode of FIG. 12 are emphasized for clarity.

As best seen in FIGS. 12 and 15e, the inventive Universal Room 100 provides a "servo-tomo" examination mode. This is a linear tomographic imaging mode. In the previously discussed imaging modes, the X-ray tube 112 and the bucky 126 or 128 remain fixed during the exposure. In contrast, in the "servo-tomo" mode, the X-ray tube 112 and the table bucky 128 move in opposite directions about an artificial fulcrum position within the patient. As is known in the art, this exposure method reveals an image of the internal structure of a planar region around the fulcrum. In this mode, the table 116 is placed in the horizontal position. The tomography control module 568, the universal control panel 160, the radiographic/fluoroscopic control module 566, the tube crane angular and longitudinal drives 576, 580, and the multi-axis motion controller 512 cooperate to move the X-ray tube head 112 and the table bucky 128 in opposed, but coordinated motion about a selected tomographic fulcrum. The fulcrum is located longitudinally at the midpoint of the table top, and vertically at an operator-selected distance from the table surface. This coordination includes directing the angular position of the X-ray tube head 112 to ensure that the X-ray beam extends through the fulcrum toward the bucky 128.

Figure 13:
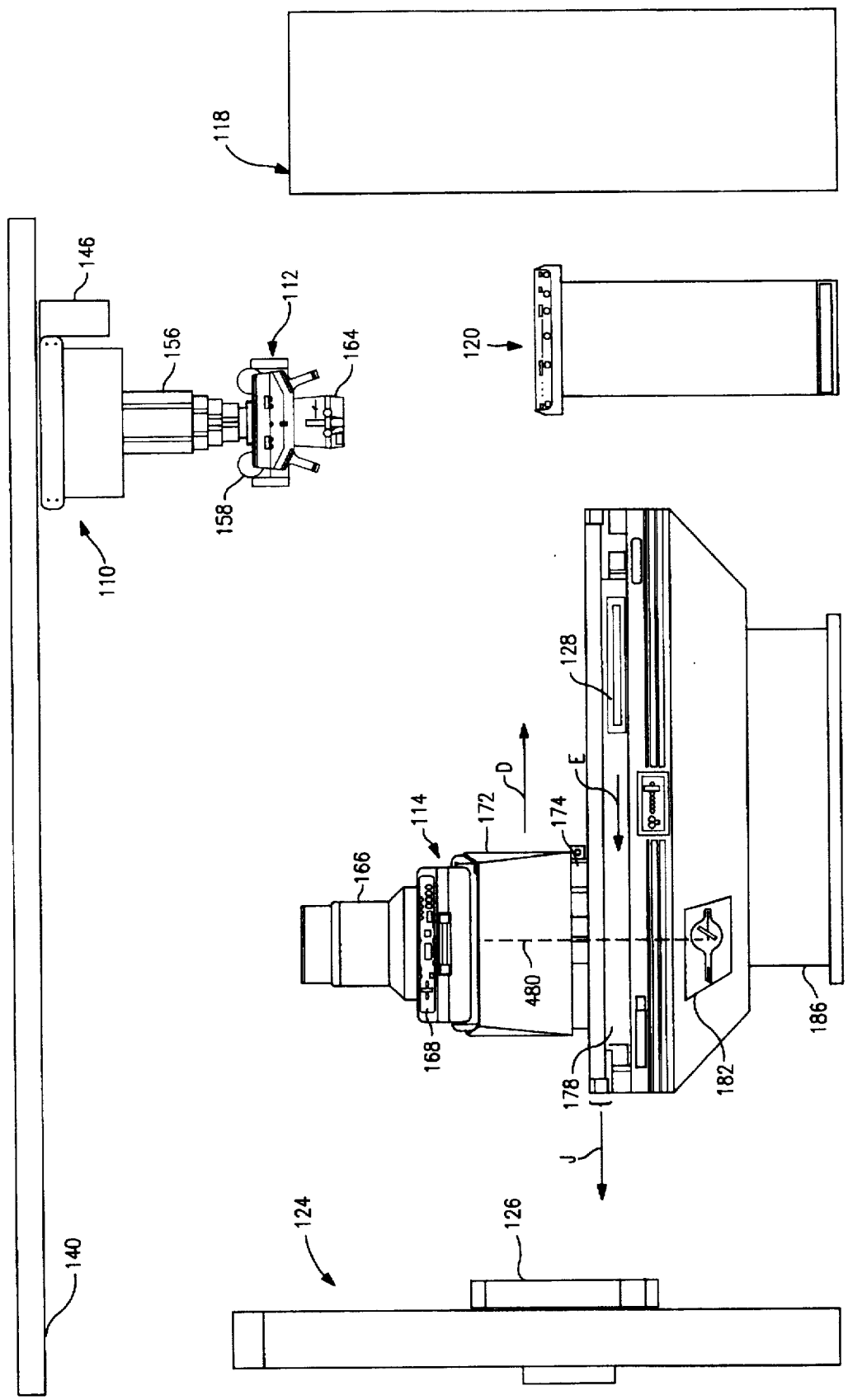
FIG. 13 is a side elevation view of the inventive Universal Room of FIG. 1, showing the coordinated movement of the digital platform tower, patient support surface, and patient table imaging cassette ("bucky") components thereof, when the Universal Room is operating in an exemplary "digital stepping" mode.

As best seen in FIGS. 13 and 15f, the inventive Universal Room 100 provides stepped digital examination modes. Such modes are particularly useful for conducting peripheral angiography examinations and certain other examinations involving fluoroscopy. These modes employ digital imaging platform 114, including the under-table X-ray tube 182, and the image intensifier 166 disposed above the table. The tube crane assembly 110 and the table bucky 128 are preferably moved out of the way to avoid mechanical and image interference. The imaging platform 114 provides a fixed geometry between the X-ray tube 182 and the image intensifier 166.

In a first digital stepping mode, a plurality of radiographic exposures at different locations in the patient's body may be obtained by causing relative motion between the patient and the imaging platform between exposures. The control system provides three operator-selectable alternatives for accomplishing relative motion between the patient and the digital platform: (1) moving the patient (using the table top-surface drive) while the digital platform 114 remains fixed; (2) moving the digital platform 114 while the patient, and table-top surface, remain fixed; or (3) simultaneously moving both the patient and digital platform 114 in opposite directions. The second alternative may be advantageous in that the patient is less subject to disturbing movements. The third alternative may be advantageous in that high relative motion speeds may be achieved while the speeds required of the patient and the digital platform are moderate.

In the stepping modes, the universal control panel 160, the radiographic/fluoroscopic control module 566, the X-ray generator control 120, the digital platform control 554, the table 116 and digital platform 114, the table angulation drive 558, the table top surface four-way drive 560, and the multi-axis motion controller 512, all cooperate to provide the coordinated relative motion between the patient and the digital platform, and to control exposure technique for optimal image quality.

One application in which it is believed that the step examination modes of the inventive Universal Room 100 will be particularly advantageous is in conducting peripheral angiography examinations, in which a contrast medium is injected in the patient's circulatory system, and the goal of imaging is to record the movement of contrast medium through the patient's body. Because the inventive Universal Room 100 allows step examinations to be conducted without moving the patient, image defects caused by patient mispositioning resulting from rapid acceleration and deceleration may be significantly reduced.

In addition, the inventive Universal Room 100 advantageously provides for test fluoroscopic examinations prior to each radiographic exposure. As is discussed further in greater detail, the test fluoroscopic examinations allow the operator to determine empirically that the contrast medium has arrived before enabling the radiographic exposure. In addition, the test fluoroscopic examinations allow automatic determination of optimal, or near optimal, technique parameters for the radiographic exposure. As a result, the inventive Universal Room 100 virtually eliminates the unusable exposures due to errors in predicting the arrival of the contrast medium which occur with prior art peripheral angiography systems. In addition, because virtually every radiographic exposure is performed with nearly optimum technique, the number of otherwise unusable exposures is sharply curtailed. As a result, the inventive Universal Room 100 substantially eliminates the need for overlapping exposures during an examination, and for complete reexaminations of the patient due to a defective initial examination. Patient radiation exposure, and the aggregate cost of performing peripheral angiography examinations, are thereby reduced.

In a second digital stepping mode, denoted the "auto-step" mode, test fluoroscopic exposures are conducted prior to each radiographic imaging exposure. Preferably, the fluoroscopic imaging system is equipped with an automatic brightness system (ABS), which adjusts at least one exposure parameter, such as X-ray tube high voltage, in order to achieve a desired consistent level of brightness and contrast in the fluoroscopic image. The exposure parameters used to conduct an exposure are referred to as the "technique." When a fluoroscopic exposure is being conducted, once the automatic brightness system has converged to a stable set of operating parameters, those parameters are recorded. Based on empirical observation or theoretical predictions, a relationship between a set of fluoroscopic technique parameters produced by the automatic brightness system, and a desirable set of technique parameters for producing an optimal radiographic exposure, can be inferred. Accordingly, the control system uses this relationship to convert the recorded exposure technique parameters for the previous fluoroscopic examination for use in performing the radiographic exposure. See, for example, "Imaging Systems for Medical Diagnostics", by Erich Krestel, Siemens Corporation, at p. 309.

In a third digital stepping mode, denoted the "auto-step-center" mode, test fluoroscopic exposures are conducted prior to each radiographic imaging exposure, and used to determine the optimal exposure technique, as in the "auto-step" mode. However, after a first fluoroscopic/radiographic exposure cycle is performed, the control system automatically determines when the contrast material is present and automatically performs the radiographic examination at the proper time. In the initial examination step, when the first radiographic exposure is enabled by the operator, indicating that the contrast medium has arrived in a desired position, the control system measures the difference in image contrast between the fluoroscopic image prior to arrival of the contrast medium and the fluoroscopic image at the time the operator enabled the radiographic exposure. This contrast difference is recorded. Then, for each subsequent examination step, during the test fluoroscopic examination portion thereof, the control system monitors the image contrast until the image contrast changes by the recorded contrast difference determined during the first examination step. The control system interprets this change in image contrast to indicate that the contrast medium has arrived, and performs the radiographic examination. The control system then proceeds to the next scheduled examination step.

The inventive Universal Room 100 provides means for the examination operator to specify, in advance, certain parameters for each step of the examination. The radiographic/fluoroscopic control module 566, the digital platform control module 554, and the digital platform control panel 168, cooperate to receive operator instructions for up to sixteen discrete steps per examination. Each examination step may include movement of the imaging position with respect to the patient, adjustment of the profile of the collimator opening, adjustment of the image intensifier magnification setting, and a radiographic exposure. If one of the automatic modes (e.g. "auto-step" or "auto-step-center") has been selected, then each step will also include an initial fluoroscopic exposure to determine technique and to ascertain whether the leading of the contrast medium has arrived in a desired position.

FIG. 16 is a diagram of an exemplary digital platform control panel 168, which may be used, inter alia to enter instructions for examinations using any of the stepping modes and to globally control certain operating parameters of the digital platform during examination. Examinations involving fluoroscopy are often conducted in a darkened room to enable operators to view image monitors and the like. Accordingly, the panel 168 is preferably illuminated such that all switches and indicators are visible in all lighting conditions. Any suitable illumination method may be used. Preferably, illumination is provided by an appropriate electroluminescent panel having an operator adjustable brightness control.

As noted above, in a preferred embodiment of the invention, the control system 510 provides up to sixteen examination steps, for which various parameters may be selected in advance. However, the preferred embodiment may be easily modified to provide additional examination steps for more complex examination regimes. Panel 168 preferably comprises a graphical display which may operate in collimator mode and a step profile mode 610 (FIG. 18). FIG. 17 is a diagram of the display 608 operating in the collimator mode in which it indicates the selected collimator opening profile for a step. FIG. 18 is a diagram of a display 610 operating in the step profile mode in which it indicates the position (with respect to the patient) and the size of the field of view, at which each of several examination steps will be conducted. Any suitable display device may be used. In a preferred embodiment, the display may be formed from a 16-element-by-16-element array of bidirectional light emitting diodes (LEDs), each of which may appear red, yellow, green, or unilluminated. In FIGS. 17–18, the display is shown as an array of boxes. The color of an illuminated LED is indicated by the letters G (green), R (red), or Y (yellow). An unilluminated LED is shown by an empty box.

In the collimator mode 608, the display shows the collimator opening which has been selected for the current examination step. Red LEDs indicate the size and shape of the selected collimator opening. Green LEDs indicate the range of available openings. Each LED corresponds to an incremental change in the collimator opening of approximately 0.25 inches. In FIG. 17, the border of green LEDs around the rectangle of red LEDs indicates that the collimator may be opened further by two increments on each side. The operator may adjust the size of the collimator opening using switches 602, which narrow or widen the collimator in the transverse direction, and switches 606, which narrow or widen the collimator in the longitudinal direction. Switch 604 toggles a mode in which the collimator opening is automatically selected by the control system. The display switch 620 enables the operator to toggle the display between the collimator mode and the step mode.

In the step profile mode, the display 610 (FIG. 18) shows the position and the size of the portion of the patient to be imaged in each examination step. Each row of the display corresponds to an image step. Each column corresponds to a longitudinal distance of 3–4 inches with respect to a starting position of the digital image platform 114. The view size (i.e. the size of the area of the patient viewed by the image intensifier) of each step is controlled by the image intensifier magnification setting for that step. The image intensifier magnification setting may be selected among "normal", "1", "2", or "3" using switch 634. Greater magnification settings result in a smaller image view. The view sizes associated with these settings depends on the size of the image intensifier; for a standard 16-inch image intensifier, the settings correspond to to view sizes of 16, 14, 12, or 9 inches, respectively. The current examination step is displayed in yellow. Previous examination steps are displayed in red. Future examination steps are displayed in green. Switches 612 allow the operator to select which step, among the sixteen available, is the current step for entry or editing of the step profile or collimator opening. Switches 618 adjust the desired longitudinal position of the exposure for the current step. Switch 614 selects among non-automatic, "auto-step," and "auto-step-center" modes of operation. Indicator 616 indicates which of these modes has been selected. The Save switch 622 causes any changes made to the current step profile to be saved.

The rabbit switch 624 enables or disables a mode in which a rapid sequence of exposures is performed. The mode switch 630 selects between a conventional stepping mode, in which a film changer 484 (FIG. 14) is used as the image rendering medium, and the digital stepping modes, in which a photospot or image intensifier 166 (FIG. 1) is used as the image rendering medium. ABS switch 638 toggles an Automatic Brightness System in which the exposure technique is automatically adjusted to provide the best image.

Angulation switches 642, 644, and 646 control the angulation (tilt) drive for table 116. Table top switches 648, 650, 652, 654, and 656 control the position of the table top surface 176. Timer reset switch 662 resets a timer which operates during fluoroscopy to limit a patient's exposure to safe levels. After a predefined period of exposure, such as five minutes, the timer expires, and fluoroscopy exposure is inhibited until the reset switch 662 is operated. The radiography control switches and indicators 664, 668, and 670, allow selection of and display certain radiographic technique parameters (specifically, X-ray tube voltage; X-ray tube current, or current-time-integral; and exposure time). The fluoroscopy control switches and indicators 672, 674, and 676 allow selection of and display certain fluoroscopic technique parameters (specifically, pulse repetition rate; X-ray tube voltage; and X-ray tube current). The compression lock switch 658 disables vertical movement of the digital platform 114. The carriage lock 660 switch disables longitudinal movement of the digital platform 114. Switches 626, 628, and 636 relate to camera functions.

Figure 19:
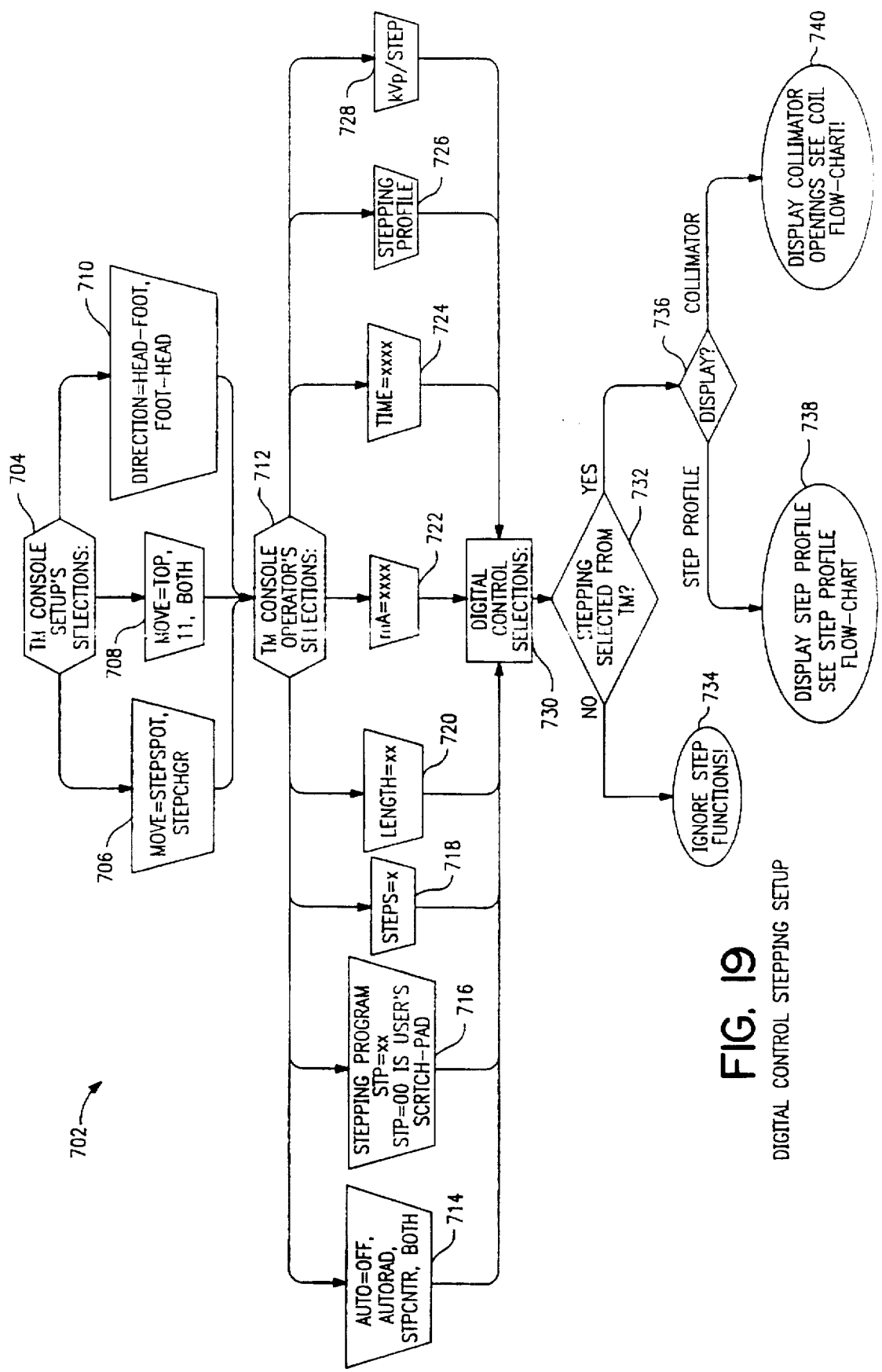
FIG. 19 is a flow chart illustrating an exemplary method of receiving operator-entered control instructions to prepare the inventive Universal Room for a combined fluoroscopic and radiographic "step" examination.

FIG. 19 is a flow diagram showing an exemplary method 702 for use by the control system of the present invention for receiving from an operator a schedule of instructions for carrying out a desired a stepping mode examination. Step 704 indicates that the first activity in setting up a step examination is to select three major operating parameters shown in steps 706, 708, 710. Steps 706, 708, and 710 represent selections input by the operator and may occur in any order. At step 706, the operator may select among a conventional stepping mode, which employs a film changer, and a digital stepping mode which employs a photospot or image intensifier for converting images to electrical signals. At step 708, the operator may select between stepping the table top only, the image intensifier (or digital platform 114) only, or both the table top and the image intensifier. At step 710, the operator may select the direction of movement of the examination. Advantageously, these selections may be entered on either of control panels 120 or 168.

Step 712 indicates that the next activity in setting up a step examination is to select among several additional operating parameters shown in steps 714–728. Steps 714–728 represent selections input by the operator which may occur in any order and, advantageously, may be entered on either of control panels 120 or 168. In step 714, the operator may select among several automatic modes for selecting exposure techniques. In step 716, the operator may select as the current step for editing one of sixteen available examination steps. In step 718, the operator may select the number of examination steps to be carried out. In step 720, the operator may select the length of the current examination step. In step 722, the operator may select a tube current for the current examination step. In step 724, the operator may select the duration of the radiographic exposure. In step 726, the operator may select the size of the area to be imaged during the current step. In step 728, the operator may select the X-ray tube voltage and the image intensifier magnification setting for use during this step.

Step 730 indicates that the next activity in setting up a step examination is to select certain additional operating parameters on the digital platform control panel 168. In step 732, the control system determines whether the stepping examination mode has been previously selected on the digital platform control panel 168. If not, the method ends at step 734, and the control system ignores attempts by the operator to control step functions using the control panel 168. If the operator has previously selected a stepping examination mode, the control system jumps to step 736, to determine whether the operator has selected the step profile or collimator display mode for display 608, 610 of control panel 168. If the operator selected the step profile display mode, then the control system performs step 738, which is shown in greater detail in FIG. 20. If the operator selected the collimator display mode, then the control system performs step 740, which is shown in greater detail in FIG. 21.

Figure 20A:
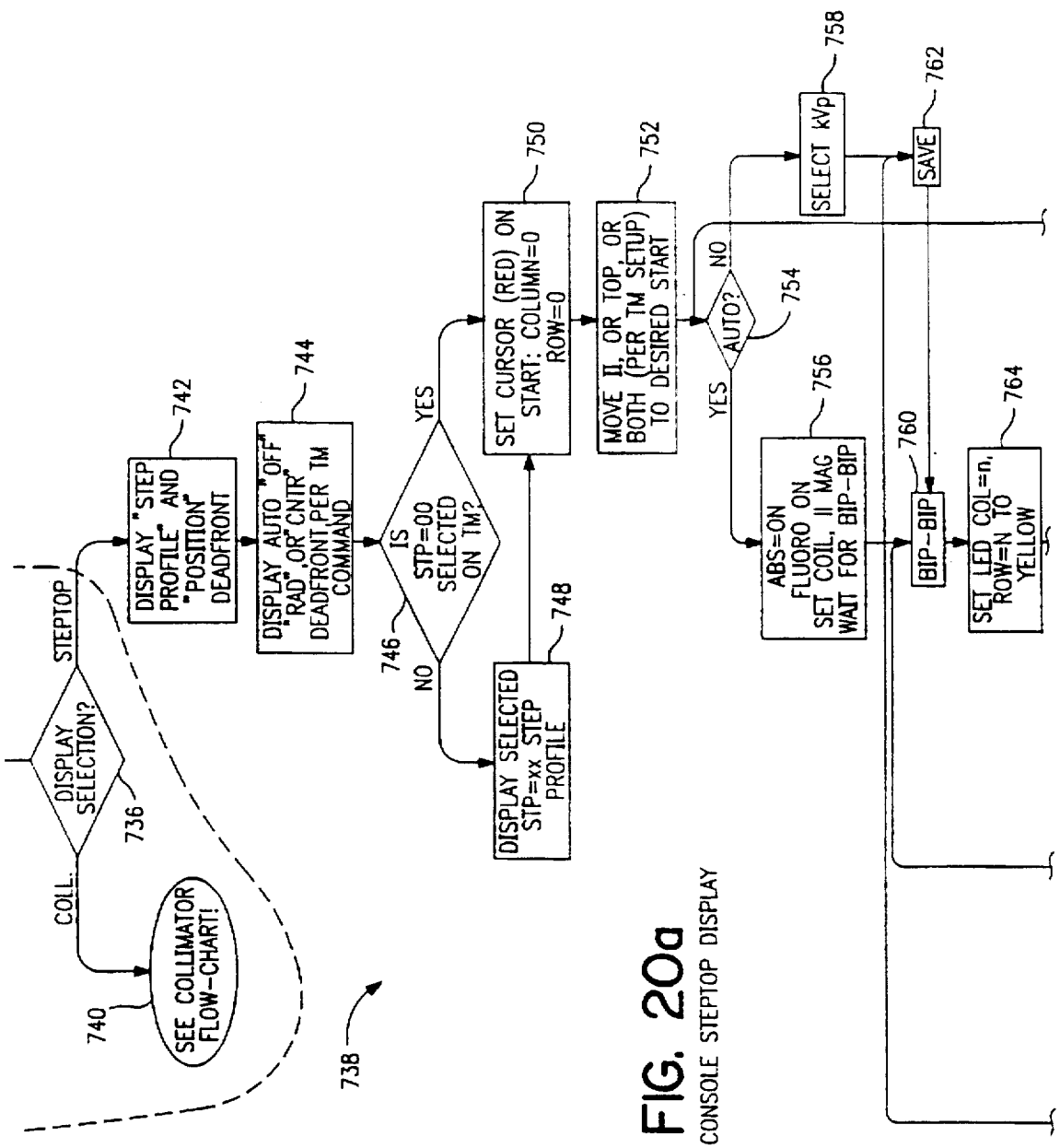
FIG. 20 is a flow chart illustrating an exemplary method of receiving operator-entered control instructions to prepare the inventive Universal Room for a combined fluoroscopic and radiographic "step" examination, showing in greater detail that portion of the method of FIG. 19 in which table positioning and exposure technique instructions for each exposure step are received.
Figure 20B:
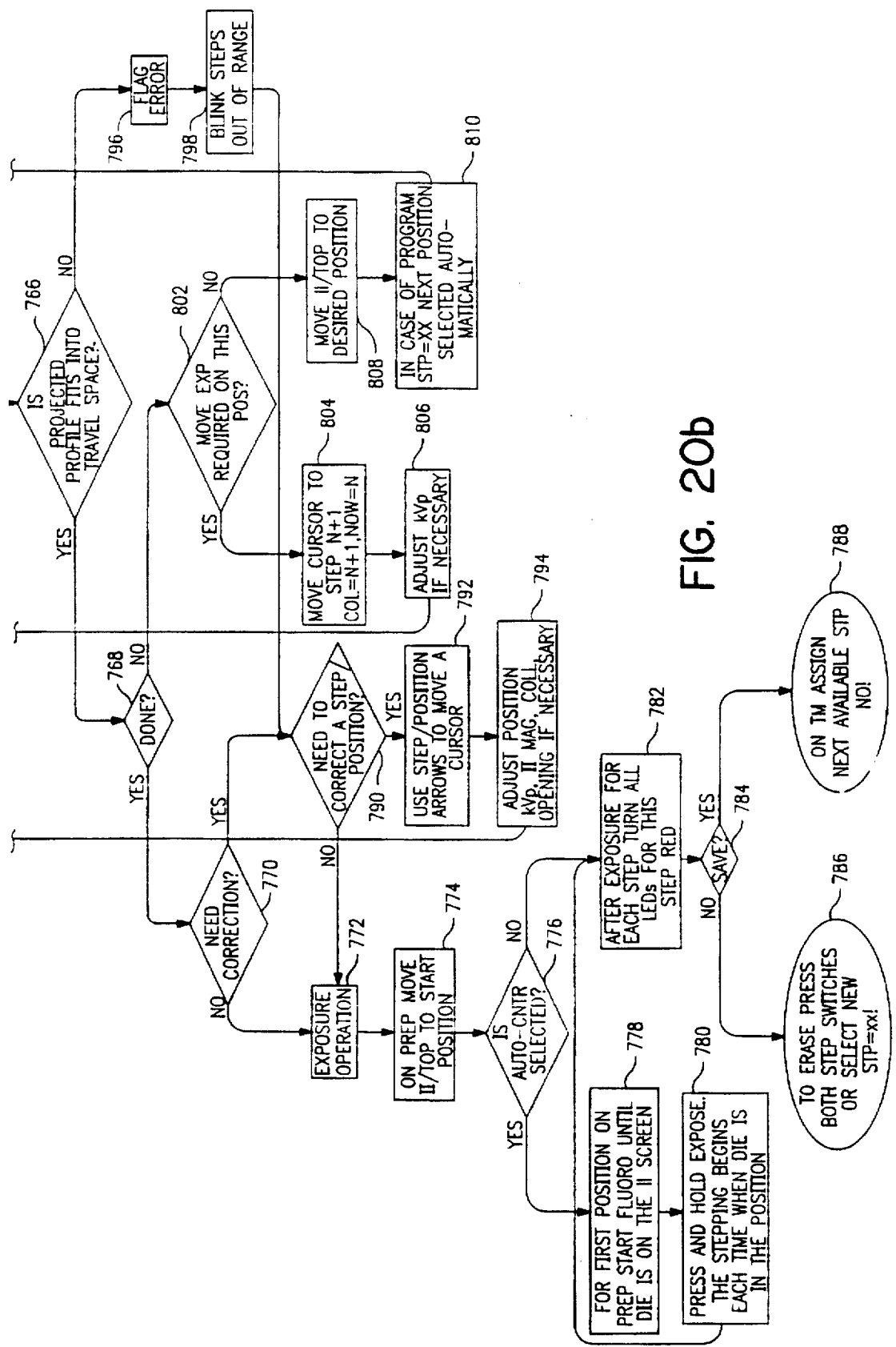

FIG. 20 is a flow diagram showing in detail a subsidiary method 738 for receiving and displaying the step profile (i.e., the imaging position and image intensifier settings) for each individual step of an examination. In step 742, illuminates "STEP PROFILE" and "POSITION" legends on the digital platform control panel 168, displays the step profile and position for the current step in display 608. In step 744, the control system displays the current stepping mode, as selected on control panels 120 or 168. In step 746, the control system determines if the current step is step 0. If the current step is not step 0, then step 748 is executed, the profile for the current step is displayed, and the method continues at step 750. If the current step is step 0, then step 750 is executed immediately. In step 750, the cursor, indicated by a red illuminated LED, is placed in the "START" position (the lower left corner) of the display 608. In step 752, the image intensifier, table top surface, or both (depending on the movement mode previously selected in step 708) to the desired examination start position.

In step 754, the control system determines whether one of the automatic technique determination modes was selected. If neither automatic mode was selected, step 758 is executed, in which the control system waits for the operator to select the X-ray tube voltage. The method then continues with step 762, in which the control system waits for the operator to press the save button. Then, the method continues with step 760. If, in step 754, one of the automatic modes was selected, step 756 is executed. The automatic brightness system is enabled, the fluoroscopy mode is enabled, the collimator and image intensifier magnification are set to the desired values according to the step profile, and the method continues with step 760.

In step 760, an audible signal is sounded to acknowledge the previous selections. In step 764, the display LED corresponding to the current imaging position is illuminated in yellow. In step 766, the control system determines whether the projected profile fits within the limits of travel of the mechanical components of the system. If the profile will not fit, then in step 796, an error is flagged, and in step 798, the display LEDs corresponding to examination steps which are out of range are blinked. The method then continues at step 790. If, in step 766, the projected profile was within the system's mechanical constraints, the method continues at step 768, in which the control system awaits action by the operator. If entry of information regarding the examination to be conducted at the current position is complete, the operator may press the "Exit" switch, and the method continues at step 770.

However, if the examination for the current position is incomplete, the operator does not press the "Exit" switch, and the method continues at step 802. The control system prompts the operator to elect whether to program an additional exposure at at the current examination position. If additional exposures are required, step 804 is executed, and the "current" step is advanced to the next available step. In step 806, the control system waits for an adjustment of the X-ray tube voltage for the current step, if necessary. The method then loops back to step 760.

If, in step 802, the operator indicated that no additional exposures are required at the current examination position, then step 808 is executed. The operator may now select the position of the digital platform 114 (image intensifier) for the next examination step. This may be accomplished by entering the position on the digital platform control panel 168, or by moving the digital platform itself to the desired location. In step 810, the current "step" is advanced to the next available step. The method then loops back to step 754.

If, in step 768, the operator indicates that entry of the current examination step is step 770 is executed. The control system prompts the operator to confirm whether the examination step just entered is correct. If the examination step was incorrect, so that a revision is required to the current step profile, the method continues with step 790. Otherwise, the method continues with step 772. At step 790, the control system determines whether the required correction relates to a step or position. If such a correction is required, then in step 792, the operator may use the Step and Position arrows 612 and 618 (FIG. 16) to move the cursor. In step 794, the operator may adjust the exposure position, X-ray tube voltage, image intensifier magnification, and collimator opening, as needed. Execution then loops back to step 762.

In step 772, the control system prepares to perform an exposure. In step 774, the control system moves the image intensifier 166 or table top surface 176 to the predefined "Start" position. In step 776, the controller determines whether the selected stepping mode is "auto-step-center". If the mode is "auto-step-center", then in step 778, the control system waits until the operator presses the "Expose" switch for a first time. When this occurs, the control system prepares the X-ray generator, X-ray tube, and other system components for an exposure. When the operator presses the "Expose" switch for a second time, the control system begins commences a test fluoroscopy examination. In step 780, the operator presses and holds the "Expose" switch when the contrast medium appears on the fluoroscopic image. Thereafter, for each scheduled examination step, the control system performs a test fluoroscopic examination, waits until it detects the contrast medium in position on the fluoroscopic image, and performs the scheduled radiographic exposure, and advances to the next scheduled step. The method continues at step 782.

If in step 776, the "auto-step-center" mode was not selected, the method jumps directly to step 782. After the radiographic exposure, the control system changes all of the LEDs in display 608 corresponding to the current step to red. In step 784, the control system waits for the operator to press the "Save" switch. If the operator presses the "Save" switch, the method continues with step 788, in which the next available step number is assigned. However, the operator may choose to erase the current step by pressing both step switches simultaneously or by selecting a new step without saving the current step. In that case, the method continues with step 786. In either case, entry of the current step is now complete.

Figure 21:
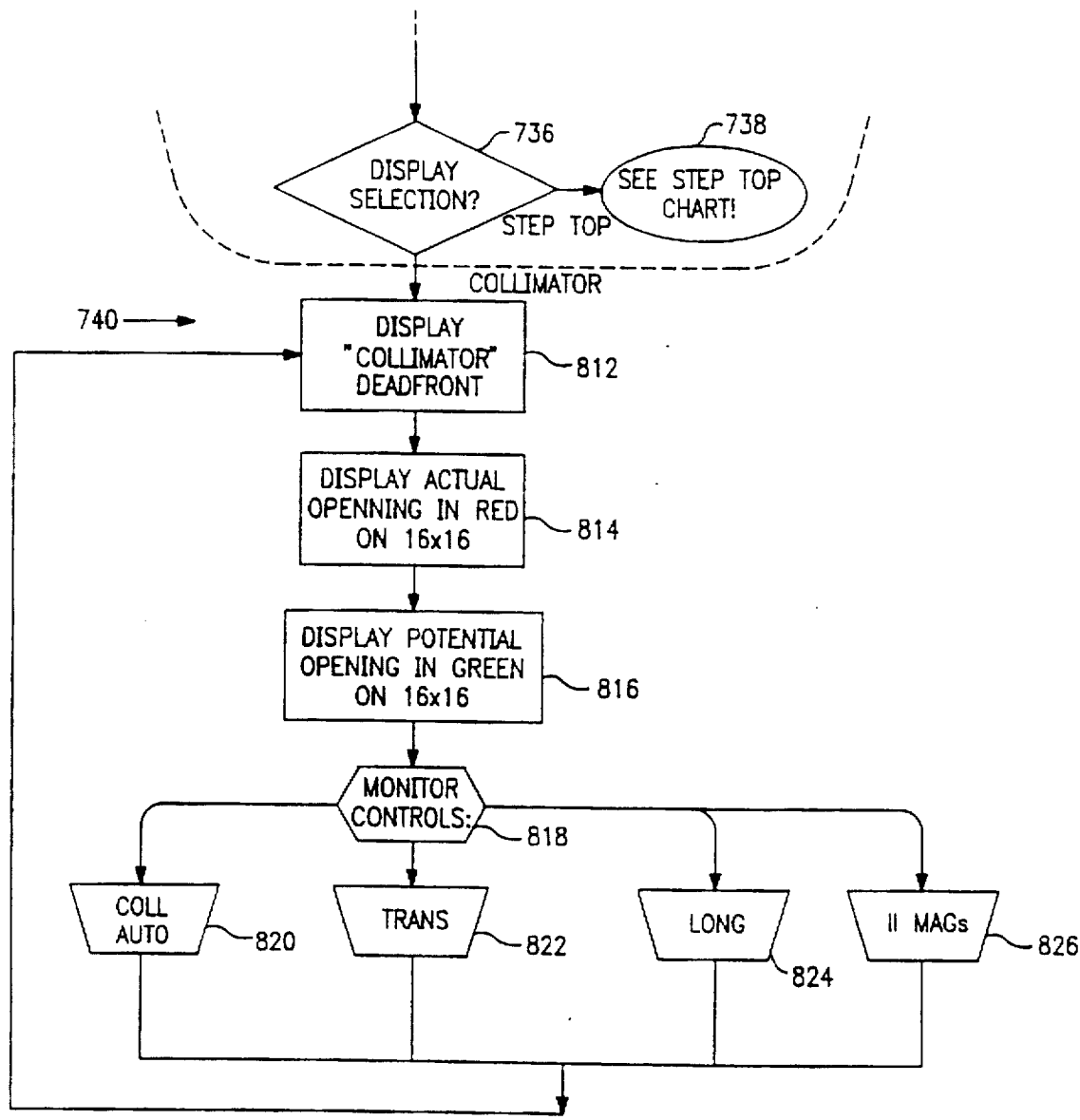
FIG. 21 is a flow chart illustrating an exemplary method of receiving operator-entered control instructions to prepare the inventive Universal Room for a combined fluoroscopic and radiographic "step" examination, showing in greater detail that portion of the method of FIG. 19 in which collimator opening instructions for each exposure step are received.

FIG. 21 is a flow diagram showing in detail a subsidiary method 740 for receiving and displaying a desired collimator opening profile for each step of an examination. In step 812, the legend "COLLIMATOR" is illuminated on the digital platform control panel. In step 814, the actual collimator opening selected for the current step is represented on display 810 by illuminating corresponding LEDs in red. In step 816, the range of permissible collimator openings is represented on display 810 by illuminating corresponding LEDs located outside of the actual collimator opening in green. In step 818, the control system monitors the control switches of the digital platform controller. Steps 820, 822, 824, and 826, represent activation by the operator of a control switch affecting the collimator opening. When the control system detects that the operator has activated one of these control switches, it performs the requested action, and loops to step 812, to update the display 810 to reflect any changes to the collimator opening caused thereby.

Figure 22:
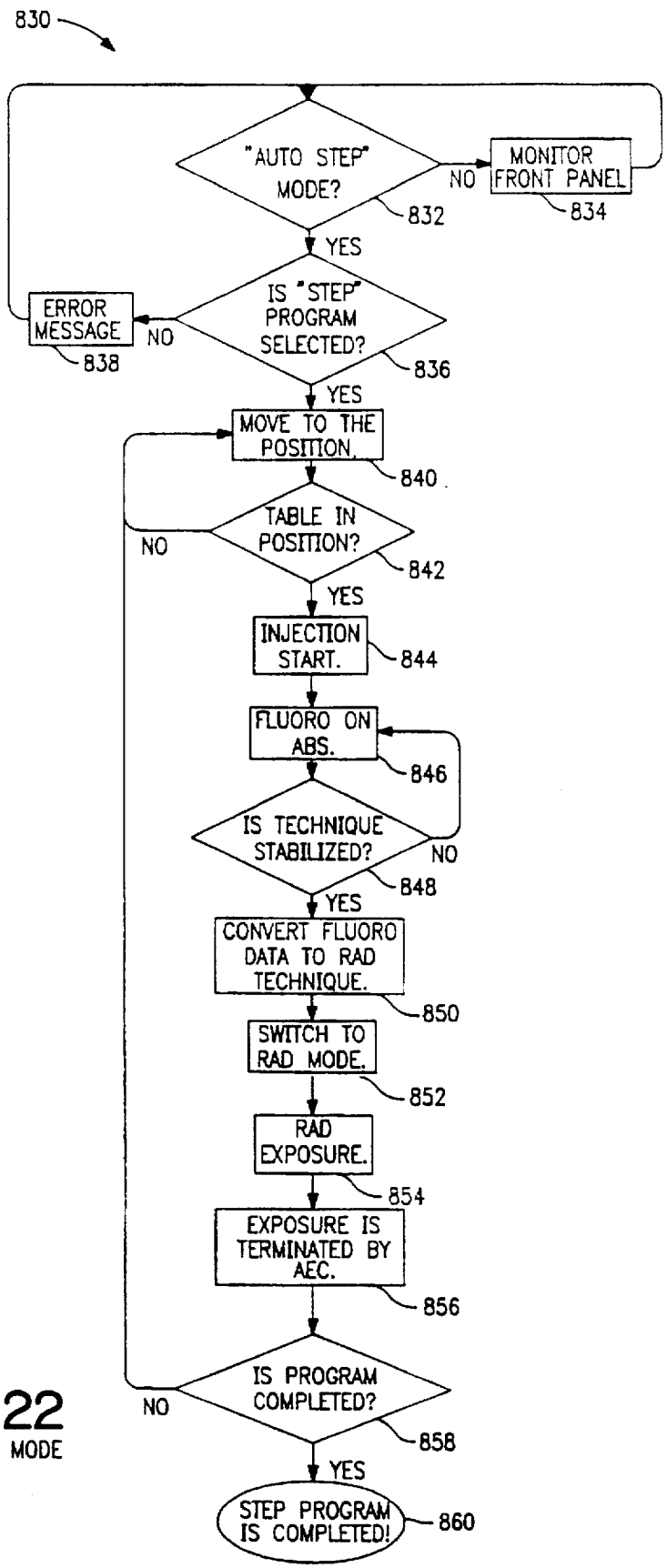
FIG. 22 is a flow chart illustrating an exemplary method of conducting a combined fluoroscopic and radiographic "step" examination, in which the inventive Universal Room operates in an "auto-step" mode.

FIG. 22 is a flow diagram of an exemplary method 830 for use by the control system of the present invention to carry out an examination in the "auto-step" mode. In step 832, the control system determines whether the selected stepping examination mode is "auto-step." If not, the method continues in step 834, in which the control panel of the digital platform is monitored, and the method loops back to step 832. In step 832, the control system determines whether a "step" program has been selected by the operator. If no "step" program has been selected, step 838 is executed, in which an error message is reported, and the method loops back to step 832.

If, in step 836, a step program was selected, then the first step thereof becomes the "current" step, and the method continues with step 840. In step 840, the control system moves the table top surface, the image intensifier, or both, as selected by the operator, to the exposure position selected for that step. In step 842, the control system checks whether the table top or image intensifier have reached the desired position. If they have not, the method loops back to step 840. If the table top or image intensifier have arrived in the proper position, step 844 is executed. The control system enables injection of the contrast medium. In step 846, the control system begins a fluoroscopic exposure, with the automatic brightness system (ABS) enabled, so that the fluoroscopic exposure will use the optimal exposure technique. In step 848, the control system determines whether the fluoroscopic exposure technique, under control of the ABS, has stabilized. If the technique has not stabilized, then the method loops back to step 846, and this loop continues until the technique becomes stable.

Once the fluoroscopic exposure technique becomes stable, step 850 is performed, in which the optimal fluoroscopic technique parameters are converted to optimal technique parameters for radiographic examination. In step 852, the system switches to radiography mode. In step 854, a radiographic exposure is commenced using the technique parameters developed in step 850. In step 856, the exposure is terminated by an automatic exposure control (AEC). In step 858, the control system examines the step program to determine whether it has been completed. If so, the auto-step method terminates at step 860. If the step program has not completed, the "current" step is advanced to the next step in the program, and the method loops back to step 840.

Figure 23A:
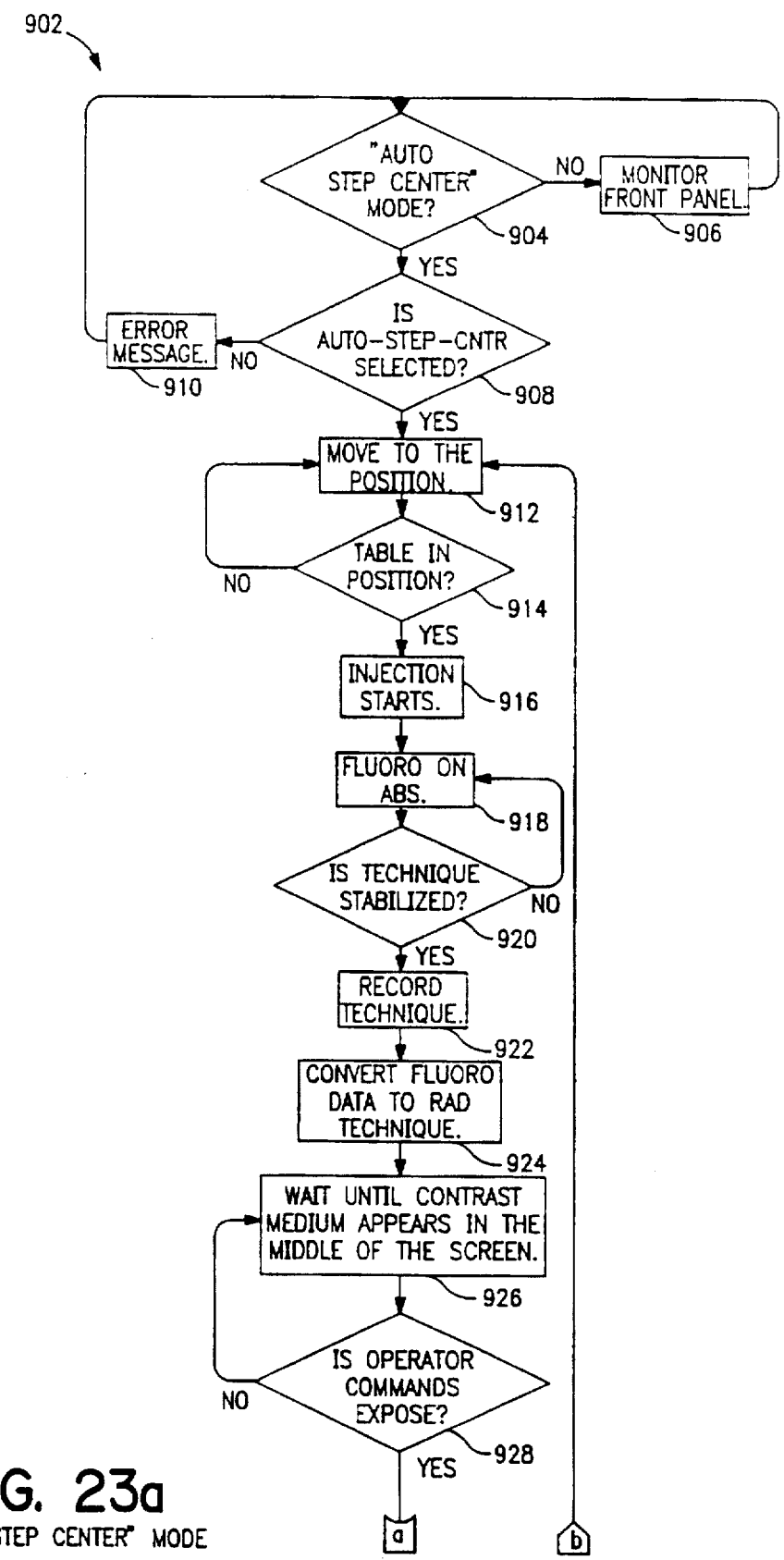
FIGS. 23a and 23b comprise a flow chart illustrating an exemplary method of conducting a combined fluoroscopic and radiographic "step" examination, in which the inventive Universal Room operates in an "auto-step-center" mode.
Figure 23B:
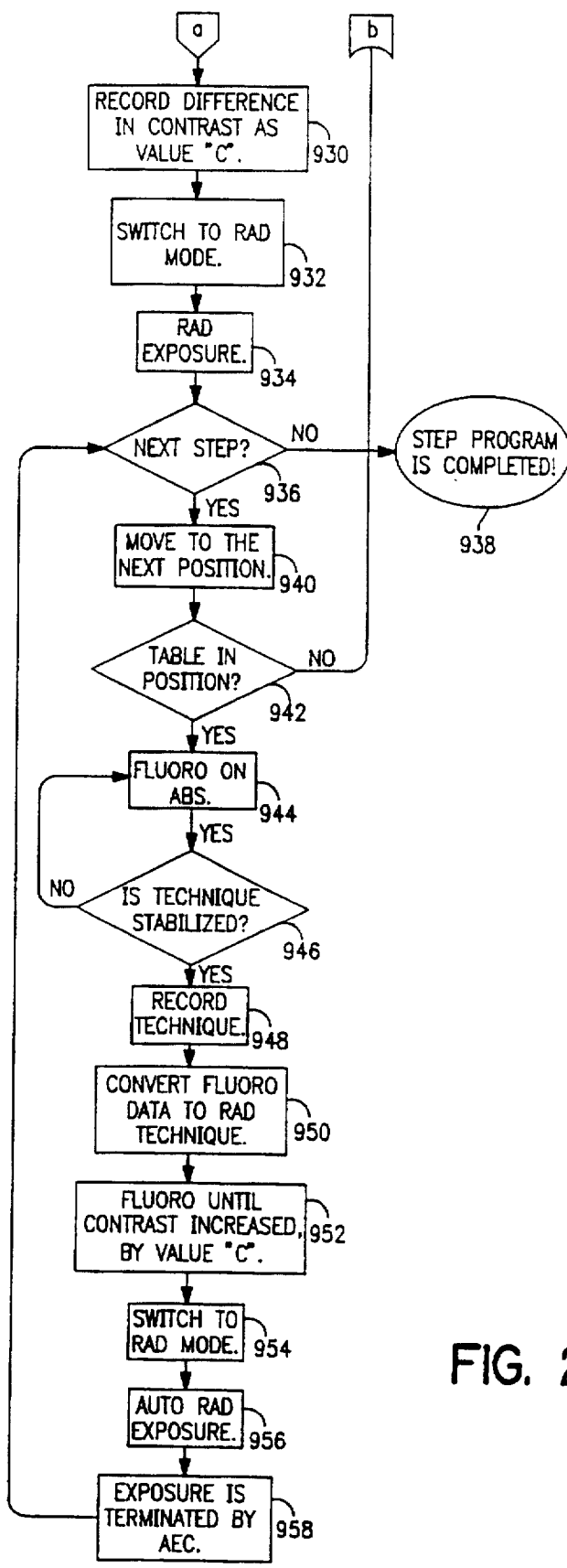

FIGS. 23a and 23b are a flow diagram of an exemplary method 830 for use by the control system of the present invention to carry out an examination in the "auto-step-center" mode. In step 904, the control system determines whether the selected stepping examination mode is "auto-step-center." If not, the method continues in step 906, control panel of the digital platform is monitored, and the method loops back to step 904. In step 908, the control system determines whether an "auto-step-center" program has been selected by the operator. If no "auto-step-center" program has been selected, step 910 is executed, in which an error message is reported, and the method loops back to step 904.

If, in step 908, an "auto-step-center" program was selected, then the first step thereof becomes the "current" step, and the method continues with step 912. In step 912, the control system moves the table top surface, the image intensifier, or both, as selected by the operator, to the exposure position selected for that step. In step 914, the control system checks whether the table top or image intensifier have reached the desired position. If they have not, the method loops back to step 912. If the table top or image intensifier have arrived in the proper position, step 916 is executed. The control system enables injection of the contrast medium. In step 918, the control system begins a fluoroscopic exposure, with the automatic brightness system (ABS) enabled, so that the fluoroscopic exposure will use the optimal exposure technique. In step 920, the control system determines whether the fluoroscopic exposure technique, under control of the ABS, has stabilized. If the technique has not stabilized, then the method loops back to step 918, and this loop continues until the technique becomes stable.

Once the fluoroscopic exposure technique becomes stable, step 922 is performed, in which the optimal fluoroscopic technique parameters produced by the ABS are recorded in a suitable memory or other storage. In step 924, the optimal fluoroscopic technique parameters are converted to optimal technique parameters for radiographic examination. Steps 926 and 928 form a loop in which the system waits until the operator observes the contrast medium in a desired location on the fluoroscopic image, and responsive thereto, activates the "Expose" switch. Once the operator activates the Expose switch, step 930 is performed. The difference "C" in image contrast between the current image, and an original image, in which no contrast medium appeared, is recorded in a suitable memory or other storage device. In step 932, the system switches to radiography mode. In step 934, a radiographic exposure is performed using the technique parameters developed in step 918 and recorded in step 922. In step 936, the control system examines the step program to determine whether any additional examination steps remain to be performed. If none remain, the auto-step-center method terminates at step 938.

However, if further examination steps remain, step 940 is performed. The next available step becomes the "current" step, and the table top surface, or the image intensifier, is moved to the desired exposure position for this new step. In step 942, the control system checks whether the table top or image intensifier have reached the desired position. If they have not, the method loops back to step 912. If the table top or image intensifier have arrived in the proper position, step 944 is executed.

In step 944, the control system begins a fluoroscopic exposure, with the automatic brightness system (ABS) enabled, so that the fluoroscopic exposure will use the optimal exposure technique. In step 946, the control system determines whether the fluoroscopic exposure technique, under control of the ABS, has stabilized. If the technique has not stabilized, then the method loops back to step 944, and this loop continues until the technique becomes stable. Once the fluoroscopic exposure technique becomes stable, step 948 is performed, in which the optimal fluoroscopic technique parameters produced by the ABS are recorded in a suitable memory or other storage.

In step 950, the optimal fluoroscopic technique parameters are converted to optimal technique parameters for radiographic examination. In step 952, the control system monitors the image contrast, and the fluoroscopic examination begun in step 944 continues until the image contrast increases by the contrast difference "C" recorded in step 930. The control system interprets this as an indication that the contrast medium is present in a desired region of the image, and therefore, performing the radiographic exposure is now appropriate. In step 954, the system switches to radiography mode. In step 956, a radiographic exposure is commenced using the technique parameters developed in step 944 and recorded in step 948. In step 958, the exposure is terminated by an automatic exposure control (AEC). The method then loops back to step 936, to determine whether any determine whether any additional examination steps remain to be performed.

Figure 14:
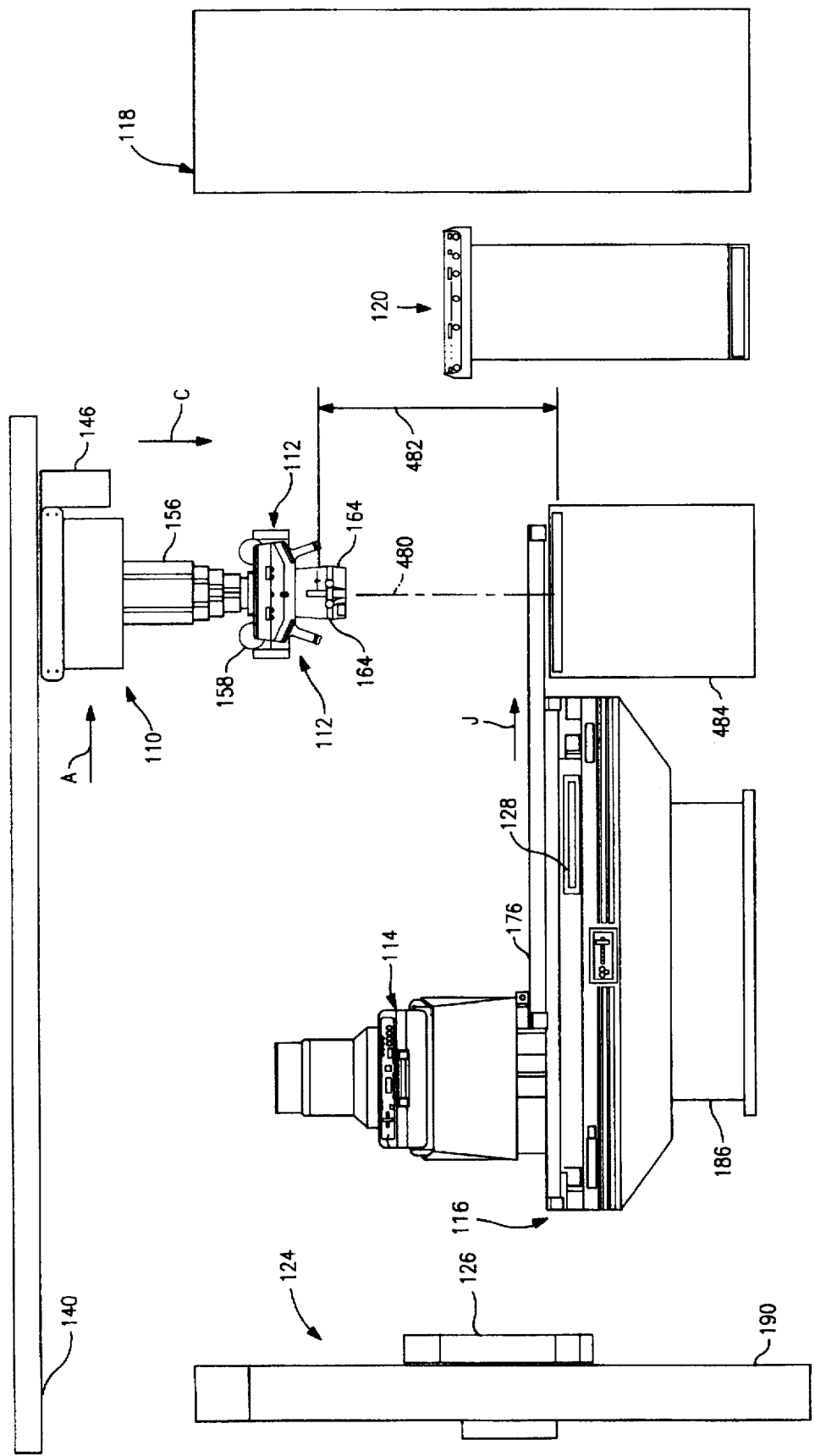
FIG. 14 is a side elevation view of the inventive Universal Room of FIG. 1, showing the coordinated movement of the tube crane and patient support surface components thereof, when the Universal Room is operating in an exemplary "film-changer stepping" mode.

As best seen in FIG. 14, the inventive Universal Room 100 also provides a stepped examination mode for use with a conventional film changer device 484. In this examination mode, the Universal Room 100 operates in a manner similar to that of a conventional peripheral angiography system. The film changer device 484 is disposed in a fixed position longitudinally adjacent an end of the table 116. The tube crane assembly 110 and X-ray tube head 112 are positioned over the film changer device such that the X-ray beam is normal to the film changer and a desired source-image-distance (SID) is maintained. Because the film changer device 484 is fixed, it is necessary to create relative motion between the patient and the film changer by moving the patient. The table top surface 176 carrying the patient is driven longitudinally so that the surface 176, and the portion of the patient to be examined, is positioned over the film changer device 484. During stepping, the control system 510 instructs the table top surface 176 four-way drive 560 to locate the patient such that the region to be examined in each step is present over the film changer device 484.

The above-described embodiments of the invention are merely examples of ways in which the invention may be carried out. Other ways may also be possible, and are within the scope of the following claims defining the invention.

What is claimed is:

1. A diagnostic imaging system adapted for selectable operation in at least radiographic, fluoroscopic, and tomographic examination modes responsive to an operator mode selection, comprising:

a movable x-ray source directed at a patient imaging position;

at least one movable x-ray recording medium;

said x-ray source and said x-ray recording medium adapted for coordinated but not mechanically interlocked movement about said patient imaging position; and means responsive to said operator mode selection for automatically causing movement of said x-ray source and said x-ray recording medium in a manner appropriate for the examination mode corresponding to said operator mode selection.

2. The imaging system of claim 1, further comprising means operable in each of said examination modes for causing movement of each of said x-ray source and x-ray recording medium to respective initial locations appropriate for said examination mode.

3. A diagnostic imaging system adapted for selectable operation in at least radiographic, fluoroscopic, and tomographic examination modes responsive to an operator mode selection, comprising:

a movable imaging energy generating means directed at a patient imaging position;

at least one movable imaging energy receiving means;

said imaging energy generating means and said imaging energy receiving means adapted for coordinated but not mechanically interlocked movement about said patient imaging position; and means responsive to said operator mode selection for automatically causing movement of said imaging energy generating means and said imaging energy receiving means in a manner appropriate for the examination mode corresponding to said operator mode selection.

4. The imaging system of claim 3, further comprising means operable in each of said examination modes for causing movement of each of said movable imaging energy generating means and said movable imaging energy receiving means to respective initial locations appropriate for said examination mode.

* * * * *

UNITED STATES PATENT AND TRADEMARK OFFICE
CERTIFICATE OF CORRECTION

PATENT NO. : 5,751,788
DATED : May 12, 1998
INVENTOR(S) : Oscar Khutoryansky, et al.

It is certified that error appears in the above-identified patent and that said Letters Patent is hereby corrected as shown below:

| | |
|---|---|
| col. 3, line 6: | delete "does" and insert --dose-- |
| col. 7, line 53: | delete "he" and insert --the-- |
| col. 7, line 59: | delete the first occurrence of "Figs." |
| col. 8, line 18: | delete "A-H, and K-L" and insert --A-L-- |
| col. 9, line 18: | delete the first occurrence of "the" |
| col. 9, line 55: | delete "Fig. 5" and insert --Fig. 15-- |
| col. 10, line 35: | after the first occurrence of "to", insert --the-- |
| col. 11, line 4: | delete "466" and insert --166-- |
| col. 11, line 8: | delete "converts 118" and insert --118 converts-- |
| col. 11, line 53: | delete "328 member" and insert --member 328-- |
| col. 11, line 59: | delete "210 assembly" and insert --assembly 210-- |
| col. 11, line 67: | after "may", insert --be-- |
| col. 12, line 4: | delete "pullies" and insert --pulleys-- |

UNITED STATES PATENT AND TRADEMARK OFFICE
CERTIFICATE OF CORRECTION

PATENT NO. : 5,751,788
DATED : May 12, 1998
INVENTOR(S) : Oscar Khutoryansky, et al.

It is certified that error appears in the above-identified patent and that said Letters Patent is hereby corrected as shown below:

| | |
|---|---|
| col. 12, line 10: | delete "pullies" and insert --pulleys-- |
| col. 12, line 18: | delete "248" and insert --340-- |
| col. 12, line 33: | delete "248 to securely lock the wheel 248" and insert --340 to securely lock the wheel 340-- |
| col. 12, line 45: | delete the first occurrence of "to" |
| col. 12, line 54: | delete the first occurrence of "is" |
| col. 13, line 22: | delete "283" and insert --298-- |
| col. 13, line 23: | delete "286" and insert --285-- |
| col. 13, line 24: | delete "284" and insert --384-- |
| col. 13, line 25: | delete "284" and insert --384-- |
| col. 13, line 28: | delete "284" and insert --384-- |
| col. 13, line 35: | delete "284" and insert --384-- |
| col. 13, line 36: | delete "284" and insert --384-- |

UNITED STATES PATENT AND TRADEMARK OFFICE
CERTIFICATE OF CORRECTION

PATENT NO. : 5,751,788
DATED : May 12, 1998
INVENTOR(S) : Oscar Khutoryansky, et al.

Page 3 of 7

It is certified that error appears in the above-identified patent and that said Letters Patent is hereby corrected as shown below:

| | |
|---|---|
| col. 13, line 45: | delete "280" and insert --281-- |
| col. 13, line 67: | delete "375" and insert --376-- |
| col. 14, line 4: | delete "390" and insert --384-- |
| col. 14, line 7: | delete "390" and insert --384-- |
| col. 14, line 8: | delete "390" and insert --384-- |
| col. 14, line 12: | delete "390" and insert --384-- |
| col. 14, line 13-14: | delete "390a and 114b" and insert --384a and 114a-- |
| col. 14, line 25: | delete "imagine" and insert --imaging-- |
| col. 14, line 57: | delete "420" and insert --416-- |
| col. 14, line 59: | delete "420" and insert --416-- |
| col. 15, line 22: | delete "546" |
| col. 16, line 45: | delete the first occurrence of "any" |
| col. 17, line 23: | delete "589" and insert --580-- |

UNITED STATES PATENT AND TRADEMARK OFFICE
CERTIFICATE OF CORRECTION

PATENT NO. : 5,751,788
DATED : May 12, 1998
INVENTOR(S) : Oscar Khutoryansky, et al.

It is certified that error appears in the above-identified patent and that said Letters Patent is hereby corrected as shown below:

| | |
|---|---|
| col. 17, line 28: | delete "126" and insert --128-- |
| col. 17, line 41: | delete "589" and insert --580-- |
| col. 20, line 13: | after "leading", insert --edge-- |
| col. 21, line 4: | delete "image" and insert --imaging-- |
| col. 21, line 13: | delete the first occurrence of "to" |
| col. 22, line 37: | after "operator", insert --has-- |
| col. 22, line 39: | after "operator", insert --has-- |
| col. 22, line 45: | delete "In step 742," and insert --Step 742-- |
| col. 22, line 48: | delete "608" and insert --610-- |
| col. 22, line 57: | delete "608" and insert --610-- |
| col. 23, line 27: | delete the first occurrence of "at" |
| col. 23, line 43: | after "step is", insert --complete, then-- |
| col. 24, line 1: | delete "begins" |

UNITED STATES PATENT AND TRADEMARK OFFICE
CERTIFICATE OF CORRECTION

PATENT NO. : 5,751,788
DATED : May 12, 1998
INVENTOR(S) : Oscar Khutoryansky, et al.

It is certified that error appears in the above-identified patent and that said Letters Patent is hereby corrected as shown below:

| | |
|---|---|
| col. 24, line 13: | delete "608" and insert --610-- |
| col. 24, line 29: | delete "810" and insert --608-- |
| col. 24, line 31: | delete "810" and insert --608-- |
| col. 24, line 39: | delete "810" and insert --608-- |
| col. 24, line 48: | delete "832" and insert --836-- |
| col. 25, line 19: | delete "830" and insert --902-- |
| col. 26, line 41: | delete "determine whether any" |

UNITED STATES PATENT AND TRADEMARK OFFICE
CERTIFICATE OF CORRECTION

PATENT NO. : 5,751,788
DATED : May 12, 1998
INVENTOR(S) : Oscar Khutoryansky, et al.

It is certified that error appears in the above-identified patent and that said Letters Patent is hereby corrected as shown below:

In the Drawings:

| | |
|---|---|
| sheet 3, Fig. 3: | delete reference no. "280", indicating the housing depicted at the upper right hand corner of the figure, and insert reference no. --281-- |
| sheet 3, Fig. 3: | delete reference no. "284", indicating the drive motor depicted left of center, beneath the housing, and insert reference no. --384-- |
| sheet 3, Fig. 3: | delete reference no. "286", indicating the mounting plate depicted left of center, adjacent the drive motor, and insert reference no. --285-- |

UNITED STATES PATENT AND TRADEMARK OFFICE
CERTIFICATE OF CORRECTION

PATENT NO. : 5,751,788
DATED : May 12, 1998
INVENTOR(S) : Oscar Khutoryansky, et al.

It is certified that error appears in the above-identified patent and that said Letters Patent is hereby corrected as shown below:

sheets 15-20,  at reference no. 536, insert the label --I/O PORTS--
Figs. 15a-f sheet 20, Fig. 15f  insert reference no. --558--, indicating the TABLE ANGULATION DRIVE WITH POSITION SENSOR Signed and Sealed this Twenty-fifth Day of August, 1998

Attest:

BRUCE LEHMAN

*Attesting Officer*  *Commissioner of Patents and Trademarks*